(12) United States Patent
Kim et al.

(10) Patent No.: US 12,725,681 B2
(45) Date of Patent: Sep. 1, 2026

(54) ELECTRONIC CHART PAGE TURNING METHOD FOR USER INTERACTION, AND COMPUTING DEVICE FOR PERFORMING METHOD

(71) Applicant: OSSTEMIMPLANT CO., LTD., Seoul (KR)

(72) Inventors: Gyu Nam Kim, Gyeonggi-do (KR); Ji Young Jang, Seoul (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 184 days.

(21) Appl. No.: 18/263,300

(22) PCT Filed: Mar. 22, 2022

(86) PCT No.: PCT/KR2022/003969
§ 371 (c)(1),
(2) Date: Jul. 27, 2023

(87) PCT Pub. No.: WO2022/203345
PCT Pub. Date: Sep. 29, 2022

(65) Prior Publication Data

US 2024/0127913 A1 Apr. 18, 2024

(30) Foreign Application Priority Data

Mar. 24, 2021 (KR) ........................ 10-2021-0038090

(51) Int. Cl.
*G16H 10/60* (2018.01)
*G06F 3/0483* (2013.01)
(Continued)

(52) U.S. Cl.
CPC ........... *G16H 10/60* (2018.01); *G06F 3/0483* (2013.01); *G06F 3/0484* (2013.01); *G06T 13/00* (2013.01); *G06F 2203/04803* (2013.01)

(58) Field of Classification Search
None
See application file for complete search history.

(56) References Cited

U.S. PATENT DOCUMENTS 8,499,251 B2 * 7/2013 Petschnigg ......... G06F 3/04883 715/776
11,389,131 B2 * 7/2022 Tuzoff ....................... G06T 7/11
(Continued)

FOREIGN PATENT DOCUMENTS

CN 112199620 A 1/2021
JP 2005025556 A 1/2005
(Continued)

*Primary Examiner* — Tuan S Nguyen
(74) *Attorney, Agent, or Firm* — Downs Rachlin Martin PLLC

(57) ABSTRACT

Disclosed are a page turning method for turning the pages of an electronic chart through a user interaction, and a computing device. The page turning method allows a user's interactive operation on an electronic chart to be sensed by considering the user's behavior of retrieving medical treatment details of a patient from a conventional paper chart, and allows pages of the electronic chart to be adjusted according to the sensed interactive operation so that a desired page of the user can be moved in the electronic chart and displayed on a screen.

19 Claims, 23 Drawing Sheets

(51) Int. Cl.

| | |
|---|---|
| ***G06F 3/0484*** | (2022.01) |
| ***G06T 13/00*** | (2011.01) |

(56) References Cited

U.S. PATENT DOCUMENTS

| | | | | |
|---|---|---|---|---|
| 2003/0048251 | A1 | 3/2003 | Liang et al. | |
| 2011/0050591 | A1* | 3/2011 | Kim | G06F 3/016 345/173 |
| 2011/0169764 | A1* | 7/2011 | Miyoshi | G06F 3/04883 345/173 |
| 2013/0232439 | A1* | 9/2013 | Lee | G06F 3/0488 715/776 |
| 2013/0268847 | A1* | 10/2013 | Kim | G06F 3/0483 715/251 |
| 2013/0339907 | A1* | 12/2013 | Matas | G06F 3/04845 715/853 |
| 2022/0308753 | A1* | 9/2022 | Song | G06F 3/04817 |

FOREIGN PATENT DOCUMENTS

| | | | |
|---|---|---|---|
| JP | 2014074982 | A | 4/2014 |
| KR | 20130070090 | A | 6/2013 |
| KR | 1020170093260 | A | 8/2017 |
| KR | 20200056176 | A | 5/2020 |

* cited by examiner

ELECTRONIC CHART PAGE TURNING METHOD FOR USER INTERACTION, AND COMPUTING DEVICE FOR PERFORMING METHOD

TECHNICAL FIELD

The present disclosure relates to a method of turning pages of an electronic chart for user interaction and a computing device performing the method, and more particularly, to a method and device for providing medical treatment details of a patient through an electronic chart based on user interaction.

BACKGROUND ART

In general, dentistry may search for and check medical treatment details of patients in an analog manner by determining the condition of a patient and recording and storing determined medical treatment details of the patient in a paper chart. A series of changes have recently occurred, and such paper medical treatment details of patients stored in paper charts have been replaced with digital electronic charts, and the electronic charts have now been provided.

However, when switching from paper charts to electronic charts while using the paper charts, there are frequent cases of returning to the existing paper charts due to the familiarity with the way the paper charts have been used for a long time and the difference in using them. In addition, as an electronic chart displays medical treatment details on a limited screen, a certain amount of time may be required to search for medical treatment details desired by a user, restricting the search and check of medical treatment details.

Therefore, there is a need for a method that may more efficiently retrieve medical treatment details desired by a user in consideration of a behavior pattern of the user who is familiar with a typical analog method.

DISCLOSURE OF INVENTION

Technical Goals

An aspect of the present disclosure may provide a device and method for improving the convenience of use by an analog behavior of a user, using an animation effect applicable to an electronic chart based on user interaction during a dental treatment.

An aspect of the present disclosure may provide a device and method for moving to a page desired by a user in an electronic chart by applying, to each page of the electronic chart, an animation effect of turning pages as in a paper chart as an organic response on a limited screen of the electronic chart according to user interaction.

Technical Solutions

According to an example embodiment of the present disclosure, there is provided a page turning method including: displaying a first page including a display area in which medical treatment details are arranged according to a medical treatment history on an electronic chart for user interaction; determining an animation effect applicable to the first page in response to an interaction motion detected on the first page; applying the determined animation effect to the first page to switch pages of the electronic chart; and displaying a second page by switching from the first page to the second page including a display area in which medical treatment details different from those of the first page are arranged, according to the animation effect applied to the first page.

The displaying of the first page may include displaying the first page in which at least one display area is grouped in response to a split screen of the electronic chart to view the medical treatment details.

The determining of the animation effect may include detecting an interaction motion applied to an edge of the display area included in the first page, and determining an animation effect for switching the first page in a different direction according to a position of the edge.

The determining of the animation effect may include determining an animation effect by which a screen switching range of a page displayed on the electronic chart is variably adjusted in response to the number of grouped display areas.

The determining of the animation effect may include determining an animation effect for switching the first page, in consideration of at least one of a separation distance between a first position at which the interaction motion is detected and a second position detected as moved on the first page based on the first position, or a moving direction.

The determining of the animation effect may include determining the number of pages to which the animation effect is to be applied, in consideration of at least one of the number of interaction motions detected on the first page or a pressure time detected after the interaction motion is detected.

The display area may be split into a plurality of areas for arranging the medical treatment details, wherein, to each of the plurality of areas, an identification number may be assigned to distinguish the medical treatment details visualized on the electronic chart based on a total number of pages.

The displaying of the second page may include displaying the second page by applying a folding effect of folding the first page according to the animation effect and by using a back side of the first page to which the folding effect is applied and another side connected to the back side.

According to another example embodiment of the present disclosure, there is provided a page turning method including: displaying a page comprising a display area in which medical treatment details are arranged according to a medical treatment history on a first display area of an electronic chart for user interaction; displaying a first oral image associated with the medical treatment details on a second display area of the electronic chart; applying an animation effect to the first oral image in response to an interaction motion detected in the second display area of the electronic chart; and displaying a second oral image by switching from the first oral image to the second oral image according to the animation effect applied to the first oral image.

The displaying on the second display area may include displaying the first oral image on the second display area in which the size of the first display area and the size of the second display area are variably adjusted in response to a split screen of the electronic chart.

The applying of the animation effect to the first oral image may include detecting an interaction motion applied to an edge of the second display area of the electronic chart, and determining an animation effect for switching the first oral image in a different direction corresponding to a position of the edge.

According to another example embodiment of the present disclosure, there is provided a computing device including a processor, wherein the processor is configured to: display a first page including a display area in which medical treatment details are arranged according to a medical treatment history in an electronic chart for user interaction; determine an animation effect applicable to the first page in response to an interaction motion detected on the first page; apply the determined animation effect to the first page to switch pages of the electronic chart; and display a second page by switching from the first page to the second page including a display area in which medical treatment details different from those of the first page are arranged according to the animation effect applied to the first page.

According to another example embodiment of the present disclosure, there is provided a computing device including a processor, wherein the processor is configured to: display medical treatment details according to a medical treatment history on a first display area of an electronic chart for user interaction; display a first oral image associated with the medical treatment details on a second display area of the electronic chart; apply an animation effect to the first oral image in response to an interaction motion detected in the second display area of the electronic chart; and display a second oral image by switching from the first oral image to the second oral image according to the animation effect applied to the first oral image.

Effects of Invention

According to an example embodiment of the present disclosure, a page turning method may improve the convenience of use by an analog behavior of a user, using an animation effect applicable to an electronic chart based on user interaction during a dental treatment.

According to an example embodiment of the present disclosure, a page turning method may move to a page desired by a user in an electronic chart by applying, to each page of the electronic chart, an animation effect of turning pages as in a paper chart as an organic response on a limited screen of the electronic chart according to user interaction.

According to an example embodiment of the present disclosure, a page turning method may display and check, on an electronic chart, a plurality of medical treatment details according to a medical treatment history of a user through split screens of the electronic chart according to a search mode of the electronic chart.

BEST MODE FOR CARRYING OUT INVENTION

Figure 1:
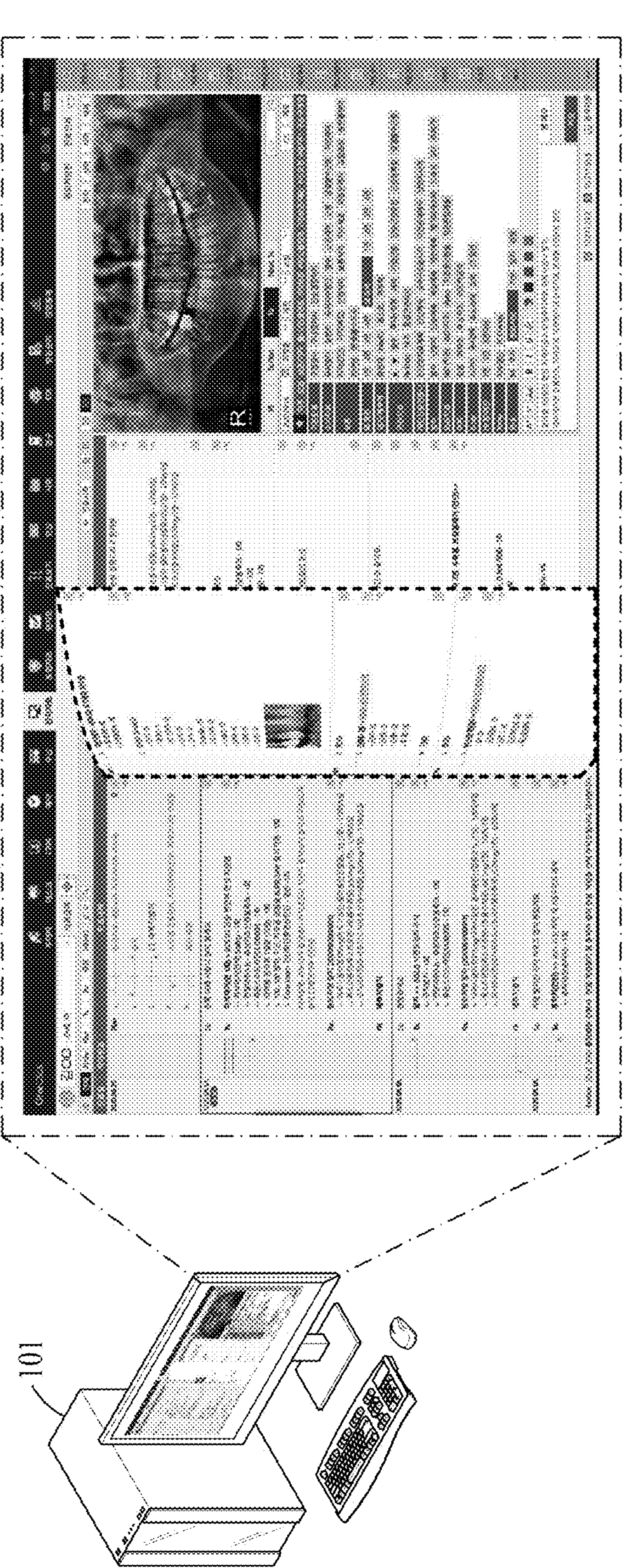
FIG. 1 is a diagram illustrating an overall configuration of switching pages of an electronic chart according to user interaction, in accordance with an example embodiment of the present disclosure.

Hereinafter, example embodiments will be described in detail with reference to the accompanying drawings. However, various alterations and modifications may be made to the example embodiments. The example embodiments are not intended to limit the scope of claims of the present disclosure. The example embodiments should be understood to include all changes, equivalents, and replacements within the idea and the technical scope of the disclosure.

The terminology used herein is for the purpose of describing particular embodiments only and is not intended to be limiting. The singular forms "a," "an," and "the" are intended to include the plural forms as well, unless the context clearly indicates otherwise. It will be further understood that the terms "comprises/comprising" and/or "includes/including," when used herein, specify the presence of stated features, integers, steps, operations, elements, and/or components, but do not preclude the presence or addition of one or more other features, integers, steps, operations, elements, components and/or groups thereof.

When describing the example embodiments with reference to the accompanying drawings, like reference numerals refer to like components and a repeated description related thereto will be omitted. In the description of example embodiments, detailed description of well-known related structures or functions will be omitted when it is deemed that such description will cause ambiguous interpretation of the present disclosure.

Hereinafter, example embodiments will be described in detail with reference to the accompanying drawings.

FIG. 1 is a diagram illustrating an overall configuration of switching pages of an electronic chart according to user interaction, in accordance with an example embodiment of the present disclosure.

Referring to FIG. 1, a computing device 101 may display medical treatment details of a patient on an electronic chart according to a search request from a user. The computing device 101 may provide an interaction design that induces the user to view the medical treatment details in consideration of a behavioral method of the user detecting medical treatment details of a patient using an existing paper chart. For example, the computing device 101 may provide a page turning method to create a digital ecosystem environment in the dental industry and increase the distribution rate of electronic charts according to the digital ecosystem environment. In addition, when providing the page turning method, the computing device 101 may analyze the most similar behavior of the user that may be shown when using a paper chart during a medical treatment, and use an analysis result obtained by the analyzing as information for providing the interaction design.

An example embodiment of the present disclosure may provide an interface that allows users who use electronic charts to actively use the electronic charts with a familiar sense when they may feel with paper charts without a separate learning process, by applying an analog sense in using an electronic chart to the digital environment in consideration of users familiar with the paper charts.

An example embodiment of the present disclosure may provide a method that improves a scrolling method used for a typical electronic chart and allows a user to view a medical treatment history, and the method may apply an animation effect of opening a paper book when providing the medical treatment history on the electronic chart. An example embodiment of the present disclosure may provide a method that allows a user to comfortably recognize an electronic chart according to an animation effect, thereby enhancing the usability of the electronic chart through combination with an interaction design. For example, the animation effect may be one of a page turning animation, a slide animation, a zoom-in animation, a zoom-out animation, a side zoom-in/zoom-out animation, a fade-out animation, a rotation animation, and a falling animation.

In addition, the computing device 101 may display, on the electronic chart, a page including a display area in which medical treatment details are arranged according to a medical treatment history based on the interaction design, thereby inducing the user to rapidly search for medical treatment details of an existing patient that are greater than medical treatment details of a new patient in terms of quantity. For example, the computing device 101 may sequentially arrange medical treatment details in at least one display area included in a page of the electronic chart, thereby inducing the user to view essential information about medical treatment details of an existing patient and establish a treatment plan within a shorter period of time.

As a result, the computing device 101 may visually deliver more information to the user by newly designing an interface or a screen navigation of the electronic chart for a medical treatment details search mode according to the convenience of use. The computing device 101 may induce the user to perform a natural behavior of turning pages of a book through the newly designed interface or screen navigation of the electronic chart.

Figure 2:
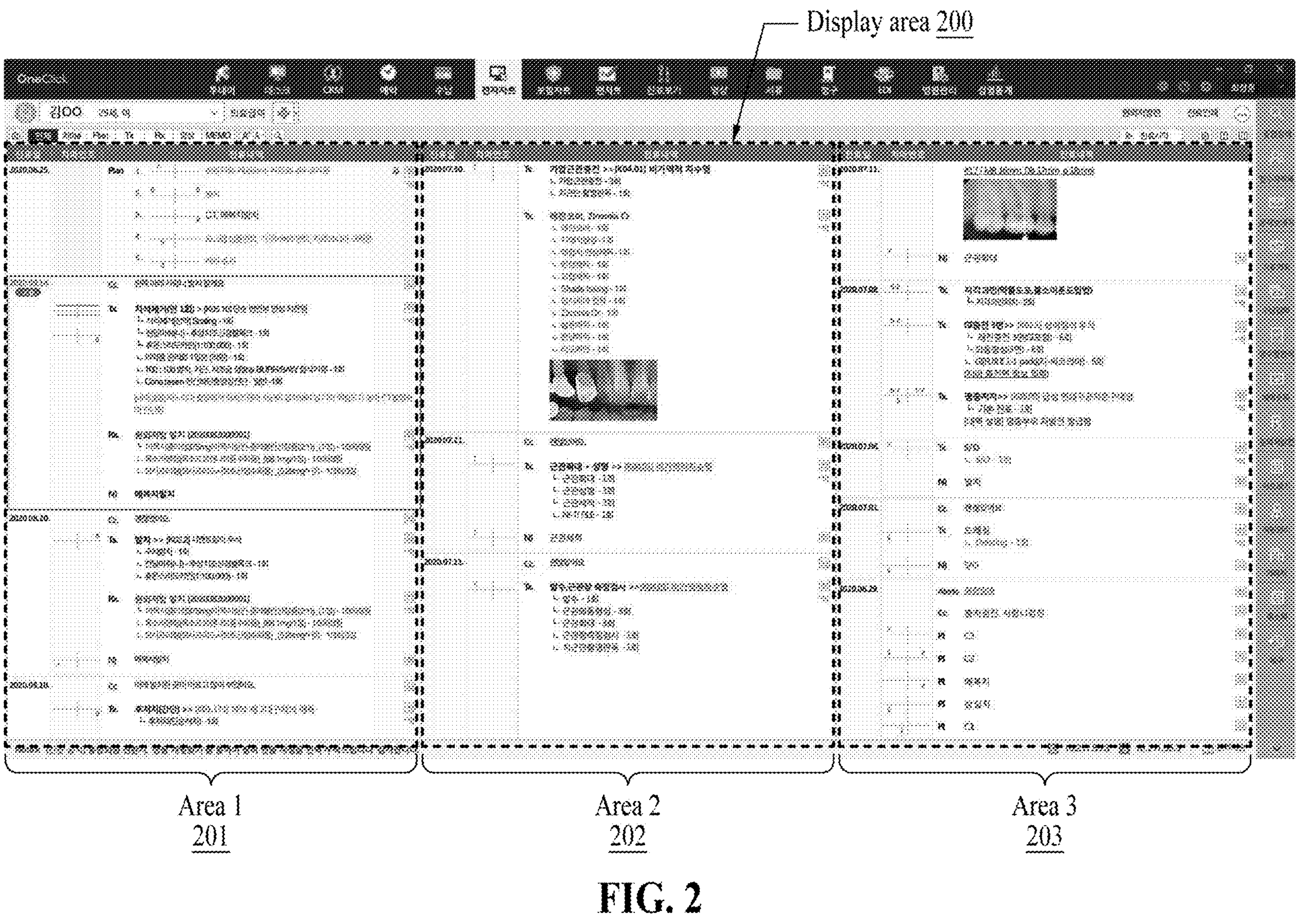
FIG. 2 is a diagram illustrating a detailed configuration of a display area included in a page of an electronic chart, in accordance with an example embodiment of the present disclosure.
Figure 3:
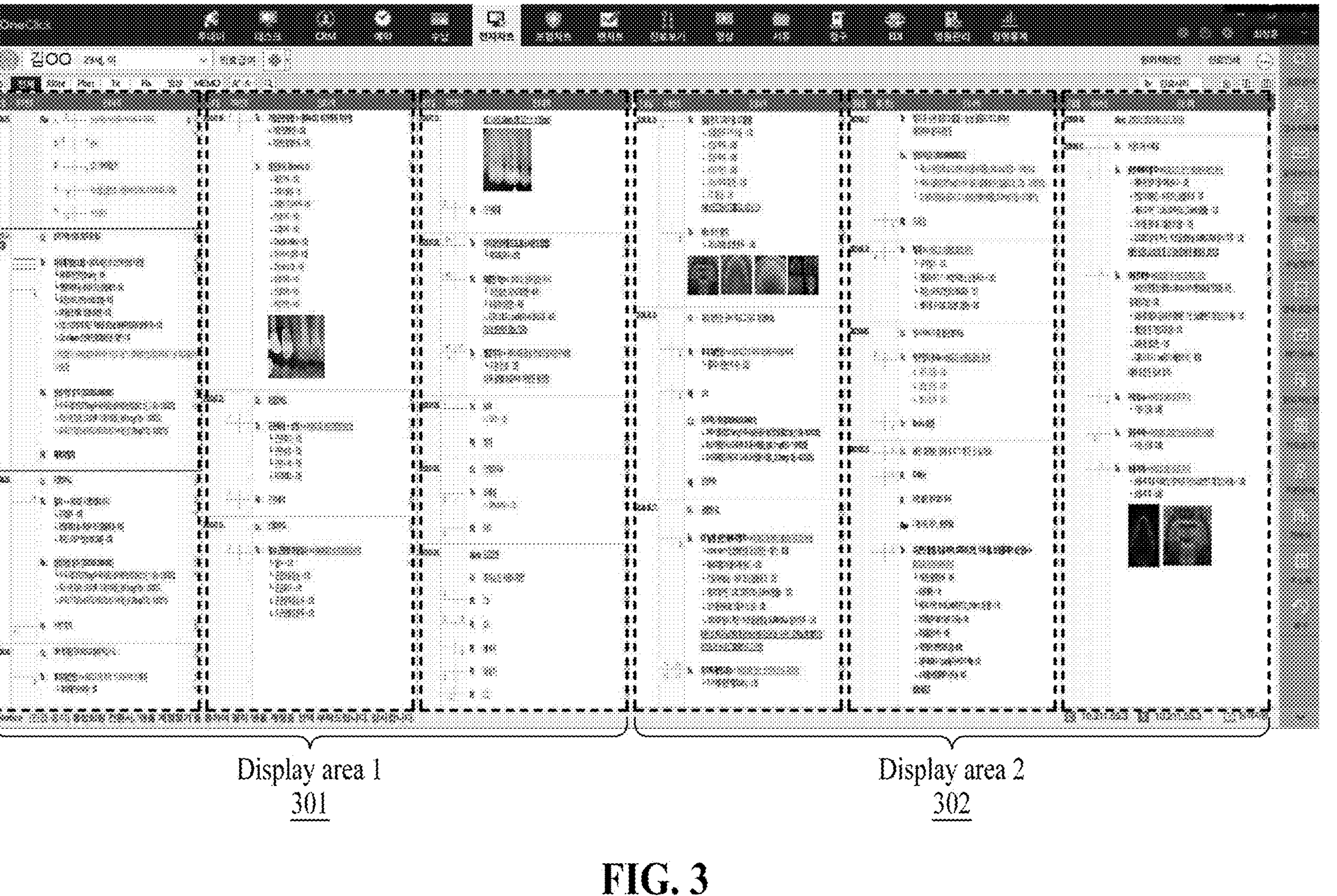
FIG. 3 is a diagram illustrating a detailed configuration of a display area included in a page of an electronic chart, in accordance with another example embodiment of the present disclosure.
Figure 4:
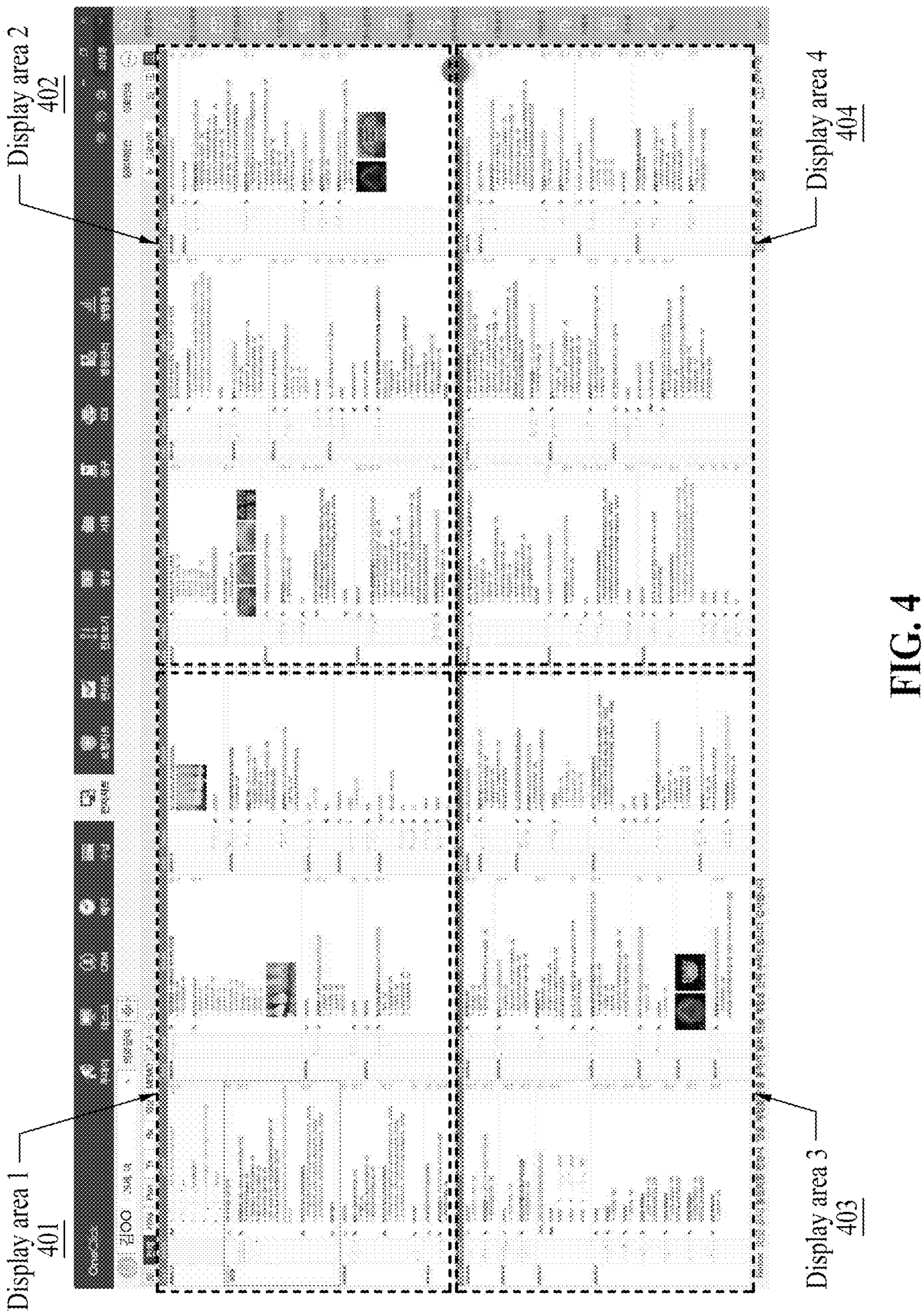
FIG. 4 is a diagram illustrating a detailed configuration of a display area included in a page of an electronic chart, in accordance with another example embodiment of the present disclosure.
Figure 5:
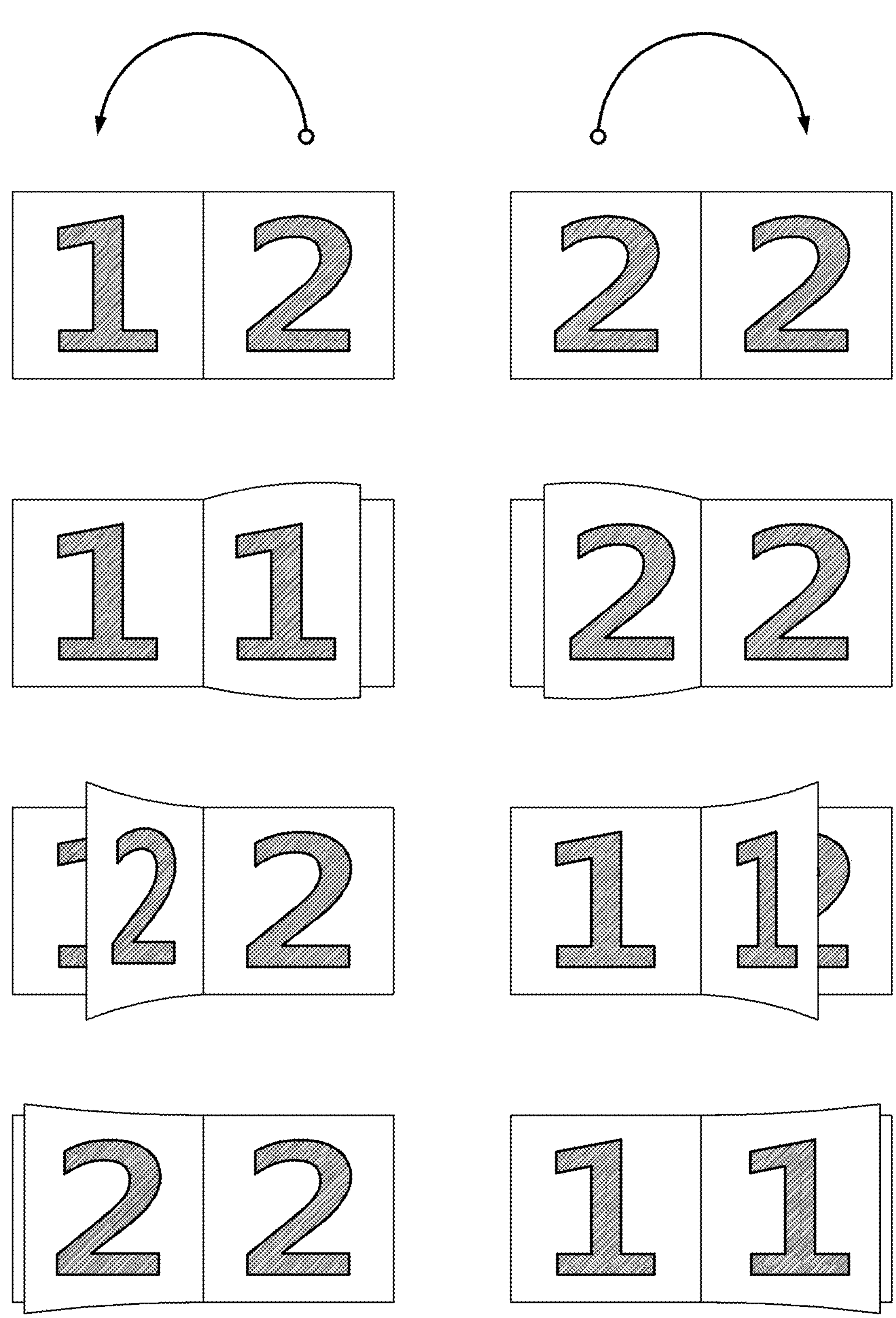
FIG. 5 is a diagram illustrating a process of displaying medical treatment details by switching pages of an electronic chart at a mouseover, in accordance with an example embodiment of the present disclosure.
Figure 6:
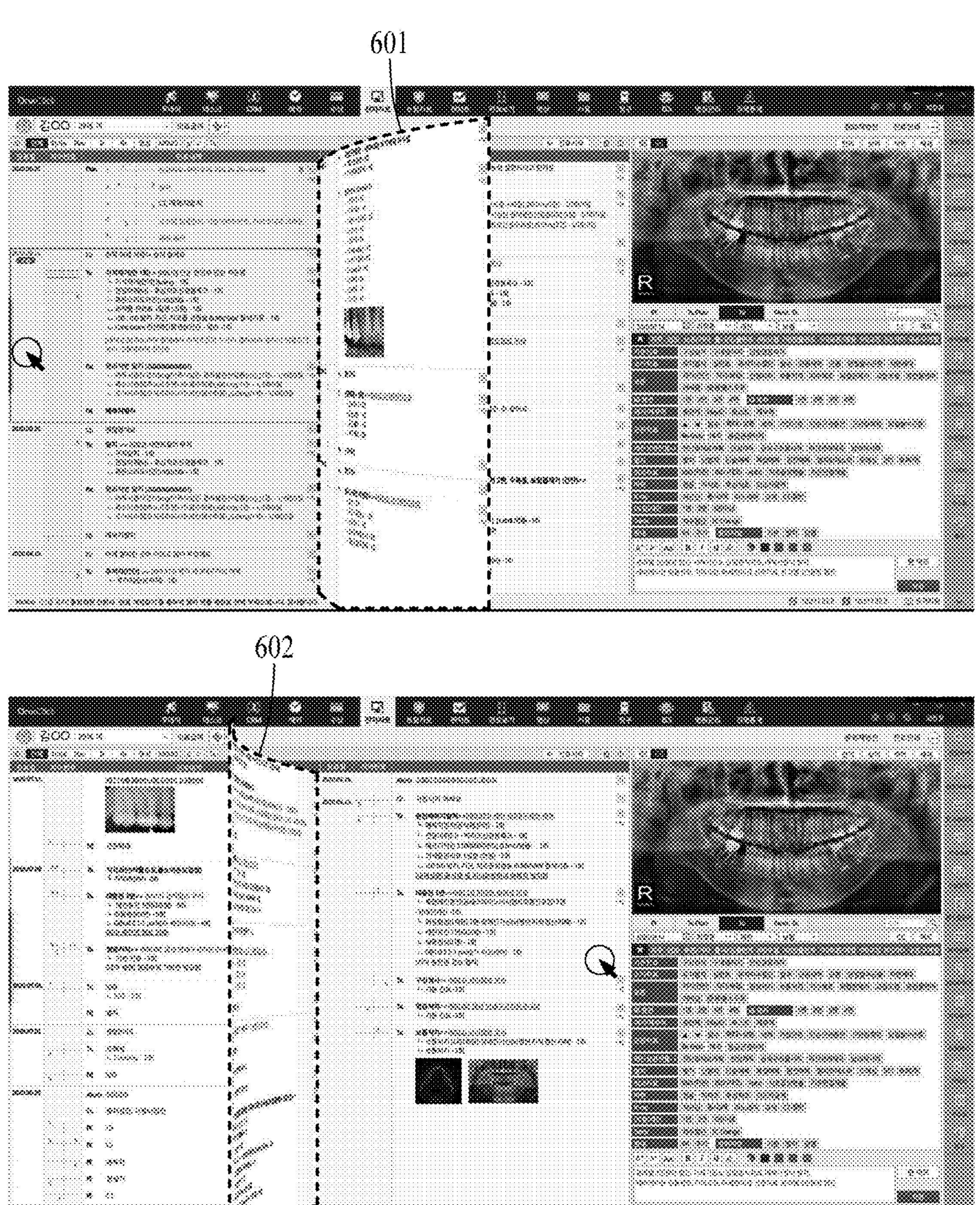
FIG. 6 is a diagram illustrating a process of displaying medical treatment details by switching pages of an electronic chart at a mouseover, in accordance with another example embodiment of the present disclosure.
Figure 7:
FIG. 7 is a diagram illustrating a process of displaying medical treatment details by switching pages of an electronic chart at a mouseover, in accordance with another example embodiment of the present disclosure.
Figure 8:
FIG. 8 is a diagram illustrating a process of displaying medical treatment details by switching pages of an electronic chart at a mouseover, in accordance with another example embodiment of the present disclosure.

FIGS. 2 to 4 illustrate a detailed configuration of a display area included in a page of an electronic chart, in accordance with an example embodiment of the present disclosure.

The computing device 101 may display, on a screen, a page including at least one display area 200 according to a search mode of an electronic chart. The display area 200 may include a plurality of areas 201, 202, and 203 to provide a user with more medical treatment details, and on the plurality of areas 201, 202, and 203, medical treatment details of a patient may be sequentially arranged according to a medical treatment history. The computing device 101 may form a minimum of one area to a maximum of three areas within the display area 200, in consideration of structural functions of information displayed on a monitor.

The medical treatment details of the patient may be arranged in at least one area corresponding to details recorded in the medical treatment history of the patient that the user desires to search for. In a case of a first-time patient or a relatively small amount of information recorded in the medical treatment history, each area of the display area 200 may be represented as a blank. For example, the computing device 101 may arrange details recorded in a medical treatment history of patient A in area 1 201 of the display area 200, and leave area 2 202 and area 3 203 blank.

The computing device 101 may configure the search mode as a split screen in which a screen is split into different numbers of screens according to the type and form of medical treatment details the user desires to search for. The search mode may represent a state in which one of one-split screen, two-split screen, and four-split screen is available to be implemented based on the display area 200.

(a) One-Split

Referring to FIG. 2, a computing device may display medical treatment details of a patient on one display area 200 including a plurality of areas 201', 202", and 203, as a split screen of an electronic chart set as a one-split screen. The computing device may display medical treatment details on the electronic chart through the three areas 201', 202", and 203 of the display area 200, thereby providing a greater amount of information than a typical electronic chart to a user.

(b) Two-Split

Referring to FIG. 3, a computing device may display a first display area 301 and a second display area 302 on an entire screen, as a split screen of an electronic chart set as a two-split screen. Each of the first display area 301 and the second display area 302 may include a plurality of areas, and successive medical treatment details may be sequentially arranged according to a medical treatment history in the plurality of areas included in the first display area 301 and the plurality of areas included in the second display area 302. The computing device may record medical treatment details according to a medical treatment history of a patient in a total of six areas according to the first display area 301 and the second display area 302 and display them on a screen of the electronic chart.

(c) Four-Split

Referring to FIG. 4, a computing device may display a first display area 401 to a fourth display area 404 on an entire screen, as a split screen of an electronic chart set as a four-split screen. Each of the first display area 401 to the fourth display area 404 may include a plurality of areas, and successive medical treatment details may be sequentially arranged according to a medical treatment history of a patient in the plurality of areas included in the first display area 401 to the fourth display area 404. The computing device may record medical treatment details in a total of 12 areas according to the first display area 301 and the second display area 302 of FIG. 3 and display them on a screen of the electronic chart.

The computing device 101 may freely reset the split screen of the electronic chart each time a split screen is necessary according to a user's search purpose, thereby providing visual effects and the convenience of searching for a medical treatment history of a patient more easily and quickly, through the split screen.

When viewing a medical treatment history of a patient as shown in FIG. 2, the computing device 101 may limit the display of medical treatment details that are viewable at one time in one display area 200, up to the three areas 201, 202, and 203. In addition, when the user views a medical treatment history according to a preset number or more split screens, the computing device 101 may provide medical treatment details through up to 12 areas, i.e., four display areas 401, 402, 403, and 404, thereby allowing the user to view essential information and establish a treatment plan for the patient in a shorter period of time.

FIGS. 5 to 8 are diagrams illustrating a process of displaying medical treatment details by switching pages of an electronic chart, in accordance with an example embodiment of the present disclosure.

Referring to FIGS. 5 to 8, the computing device 101 may display a first page (e.g., 601, 701, and 801) including a display area in which medical treatment details are arranged according to a medical treatment history in an electronic chart for user interaction. The computing device 101 may determine an animation effect that is applicable to the first page (e.g., 601, 701, and 801) in response to an interaction motion detected on the first page (e.g., 601, 701, and 801). The interaction motion, which is a motion performed by a user to view medical treatment details, may be a motion performed to switch pages of the electronic chart and may include, for example, a touch, a drag, or like applied to a certain area of a screen by the user.

The computing device 101 may determine the animation effect to switch the first page (e.g., 601, 701, and 801), in consideration of at least one of a separation distance between a first position where the interaction motion is detected and a second position detected after a movement from the first page (e.g., 601, 701, and 801) with respect to the first position, or a moving direction.

(a) Separation Distance

The computing device 101 may adjust the number of switchable pages or a page switching speed based on the separation distance between the first position and the second position. For example, the computing device 101 may calculate the separation distance between the first position and the second position. When the calculated separation distance exceeds a preset threshold, the computing device 101 may increase the number of pages or increase the speed at which the first page (e.g., 601, 701, and 801) is switched on the screen, based on the excess. Conversely, when the calculated separation distance does not exceed the preset threshold, the computing device 101 may maintain the number of switchable pages or reduce the speed at which the first page (e.g., 601, 701, and 801) is switched.

(b) Moving Direction

The computing device 101 may set a page switching direction of a page to be interacted with in response to a moving direction (or path) indicated by the first position and the second position. That is, the computing device 101 may set the page switching direction corresponding to each of the left, right, up, down, and diagonal directions that are movable on the screen. For example, referring to FIG. 4, when detecting a first position associated with an interaction motion in display area 4 404 in an electronic chart and detecting a second position associated with the interaction motion in display area 1 401 in the electronic chart, the computing device 101 may set a direction that connects the first position and the second position, i.e., a page switching direction that moves diagonally from right to left.

The computing device 101 may apply the determined animation effect to the first page (e.g., 601, 701, and 801) to switch pages of the electronic chart. The computing device 101 may switch from the first page (e.g., 601, 701, and 801) to a second page (e.g., 602 and 702) including a display area in which medical treatment details different from those of the first page (e.g., 601, 701, and 801) are arranged, according to the animation effect applied to the first page (e.g., 601, 701, and 801). The computing device 101 may display the second page (e.g., 602 and 702) by page switching.

The computing device 101 may determine an effect of displaying medical treatment details on both sides or on a single side, in consideration of a reference position for applying the animation effect onto the electronic chart. The reference position may be a page switching point on a screen to which an animation effect of, for example, turning a book, is applied. When applying the animation effect according to user interaction, the computing device 101 may consider whether to display the medical treatment details on both sides or on a single side. That is, the computing device 101 may variably adjust a screen switching range of a page to be displayed on the electronic chart according to the reference position, based on the number of display areas included in the page.

(a) Display on Both Sides

When displaying medical treatment details on both sides, the computing device 101 may adjust the screen switching range according to the reference position to be half of the page. A center position of the reference position may be adjusted according to an aspect ratio occupied by the page on the electronic chart. For example, at a mouseover as shown in FIG. 6B, the computing device 101 may display the page of the electronic chart through a display area split into two. In addition, at a mouseover as shown in FIG. 7C, the computing device 101 may display the page of the electronic chart through a display area split into 12.

In this case, the computing device 101 may apply a folding effect of folding the first page according to the animation effect, and display the second page (e.g., 602 and 702) using a back side of the first page to which such a folding effect is applied and another side connected to the back side.

(b) Display on a Single Side

When displaying medical treatment details on a single side, the computing device 101 may adjust the screen switching range according to the reference position to be full on the page. In this case, the reference position may be adjusted according to a switching direction of an interaction motion. That is, a center position of the reference position may be adjusted according to an edge of a display area included in a first page (e.g., 301). For example, at a mouseover as shown in FIG. 8D, the computing device 101 may display the page of the electronic chart through the display area split into three.

The computing device 101 may naturally switch to a page desired by the user according to user interaction. That is, the computing device 101 may apply both a direction of turning from a current page to a previous page and a direction of turning from the current page to a next page. For example, the computing device 101 may visually display a medical treatment history according to user interaction, by applying an animation effect by which the first page disappears from right to left or an animation effect by which the first page is unfolded from left to right according to each direction. Therefore, according to an example embodiment of the present disclosure, it is possible to allow a user to freely switch to a previous page or a next page based on a current page and easily search for information desired by the user.

In addition, when a page to be switched is determined in response to user interaction, the computing device 101 may display some information of medical treatment details recorded on the page to be switched, together with a page to which an animation effect is applied, using a thumbnail image or a speech bubble. For example, under the assumption that a current page is "page 3" and is to be switched to a next page which is "page 4," the computing device 101 may generate a thumbnail image or a speech bubble including all or part of medical treatment details of "page 4," such as, for example, the latest recent medical treatment date or a prescription, of medical treatment details to be displayed on "page 4." The computing device 101 may display the generated thumbnail image or speech bubble together with the page to which the animation effect is applied, thereby allowing the user to infer or check in advance the medical treatment details for the next page to be switched.

Figure 9:
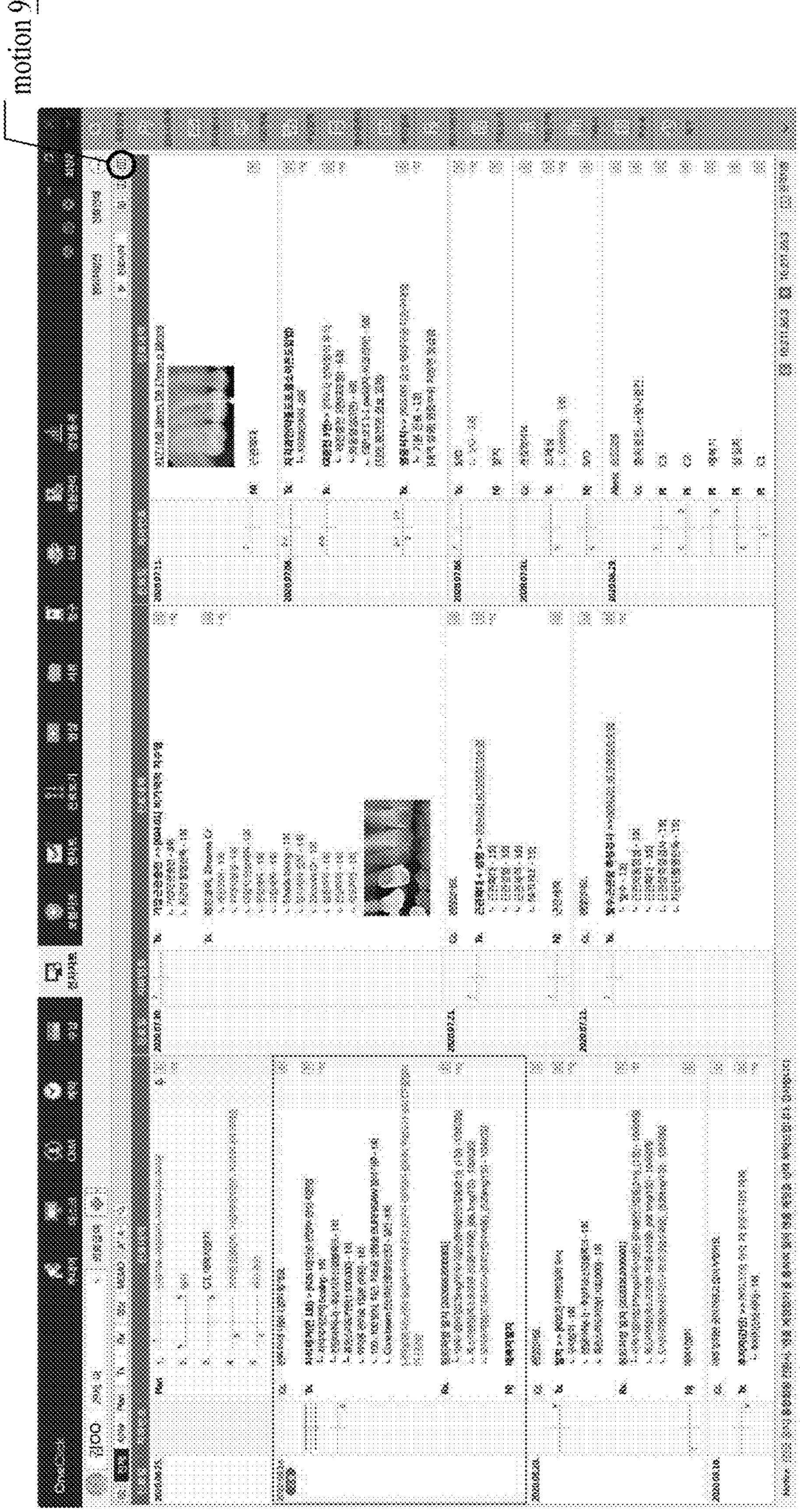
FIG. 9 is a diagram illustrating an operation of detecting an interaction motion of a user applied to a page of an electronic chart, in accordance with an example embodiment of the present disclosure.
Figure 10:
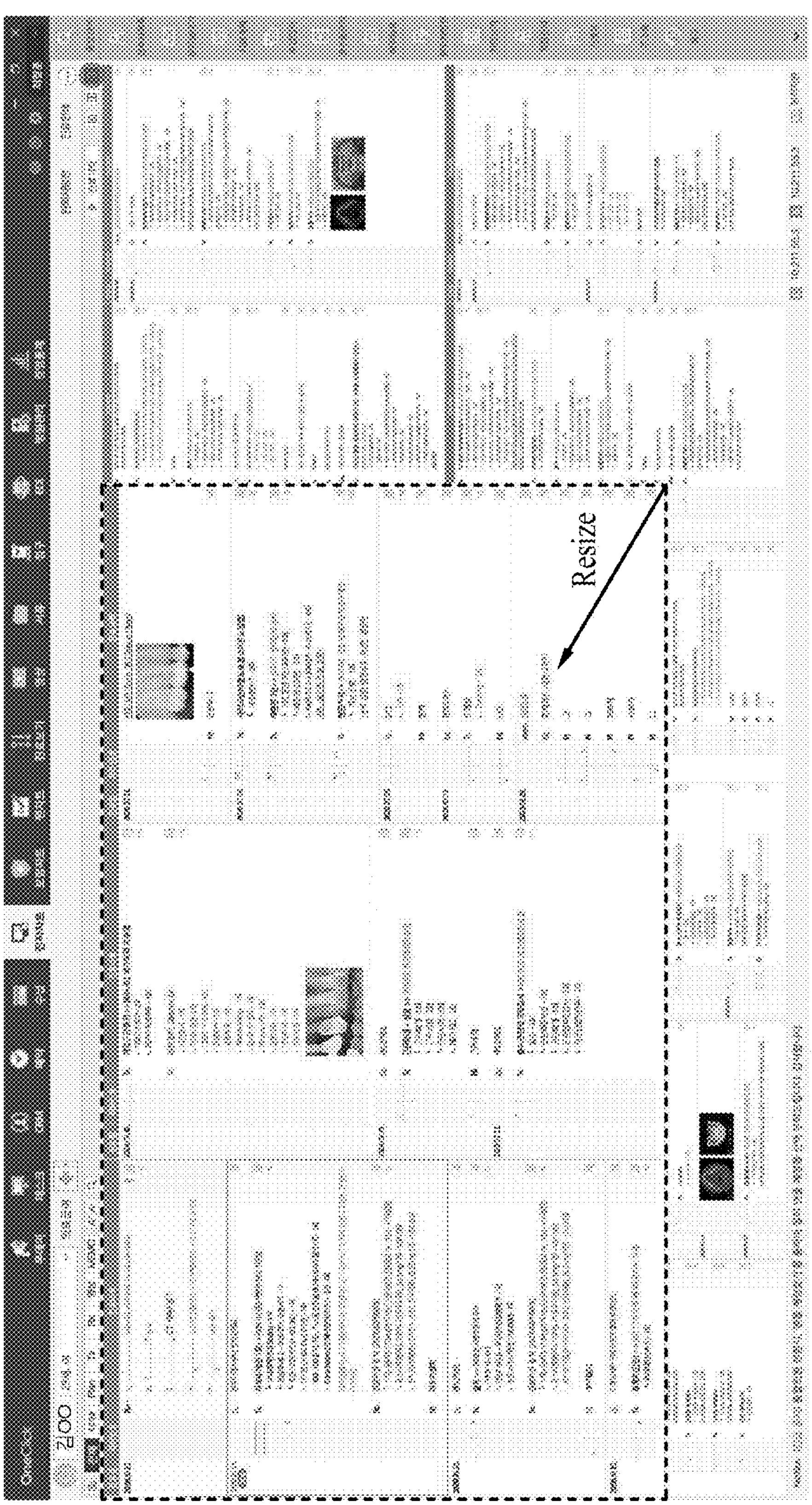
FIG. 10 is a diagram illustrating a process of adjusting the size of a display area according to a preset ratio based on an interaction motion, in accordance with an example embodiment of the present disclosure.
Figure 11:
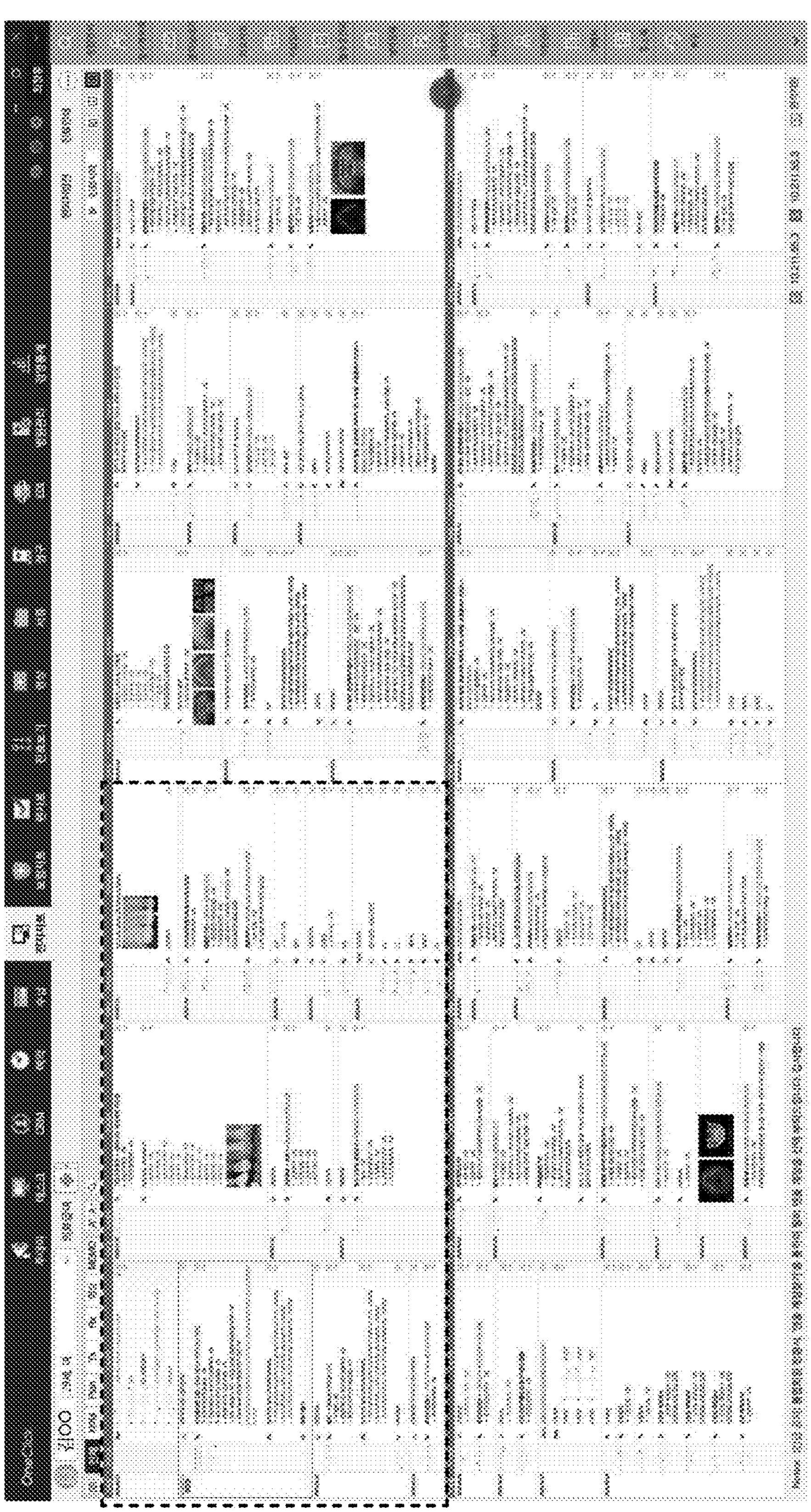
FIG. 11 is a diagram illustrating an example of displaying medical treatment details on split screens of an electronic chart by adjusting the size of a display area, in accordance with an example embodiment of the present disclosure.

FIGS. 9 to 11 are diagrams illustrating an operation of detecting an interaction motion of a user applied to a page of an electronic chart, in accordance with an example embodiment of the present disclosure.

Referring to FIG. 9, the computing device 101 may detect an interaction motion 901 detected on a first page. The interaction motion 901 may be a motion performed to select a split icon inserted in an electronic chart for splitting a split screen of an electronic chart or a click motion applied to the first page. In this case, the click motion may be classified as a double click or a right click of a mouse, or the like, which is different from a motion for applying an animation.

The computing device 101 may determine an animation effect applicable to the first page in response to the interaction motion 901 detected on the first page. In this case, the computing device 101 may determine the animation effect by which the size of a display area is adjusted according to a preset ratio according to the interaction motion 901, as shown in FIG. 10.

The animation effect by which the size of the display area is adjusted, which is an effect for increasing the efficiency of an operation of viewing medical treatment details, may switch a page to allow a user to view full and in detail. The full view may be a state in which four display areas are displayed on a page as shown in FIG. 4 and may allow the user to view or check a visual overall change in medical treatment details according to a medical treatment history. In addition, the detailed view may be a state in which one display area is displayed on a page as shown in FIG. 2 and may allow the user to view or check in detail medical treatment details of a medical treatment history required by the user.

The computing device 101 may freely switch pages of the electronic chart to enable the full or detailed view according to an interaction motion detected on the first page. In this case, the computing device 101 may move to a page desired by the user in the electronic chart and display the page on the screen by reducing or enlarging the size of the page available for the detailed view according to the interaction motion.

When the computing device 101 adjusts the size of a page from the detailed view to the full view, a display area or page may be displayed according to an element included in a page of the electronic chart. That is, as shown in FIG. 2, an arrangement of corresponding medical treatment details may be displayed as a page. However, as shown in FIG. 11, when the size of a page is adjusted and displayed on different split screens, a display area of the page may be displayed, and the display area and the page may be mixed (compatible) according to a format of display on the electronic chart according to an interaction motion.

When switching a page to the detailed view or the full view, the computing device 101 may generate a second page including medical treatment details different from those included in the first page. In a process of switching the first page according to an animation effect, the computing device 101 may display the second page overlapping the first page, in the form of a background for the first page to which the animation effect is applied, thereby maximizing an effect of switching the page.

Figure 12:
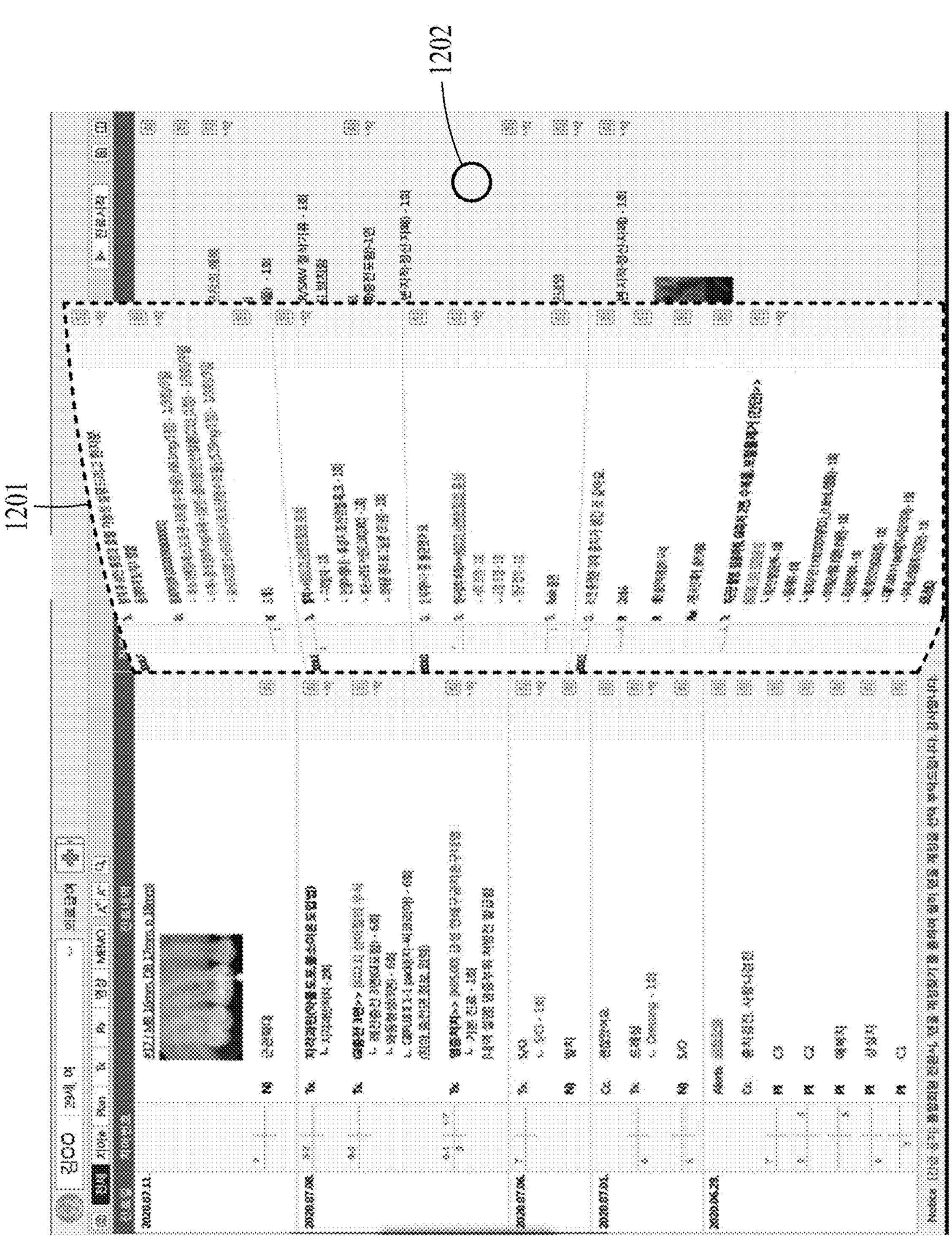
FIG. 12 is a diagram illustrating a process of switching a plurality of pages according to an interaction motion, in accordance with an example embodiment of the present disclosure.
Figure 13:
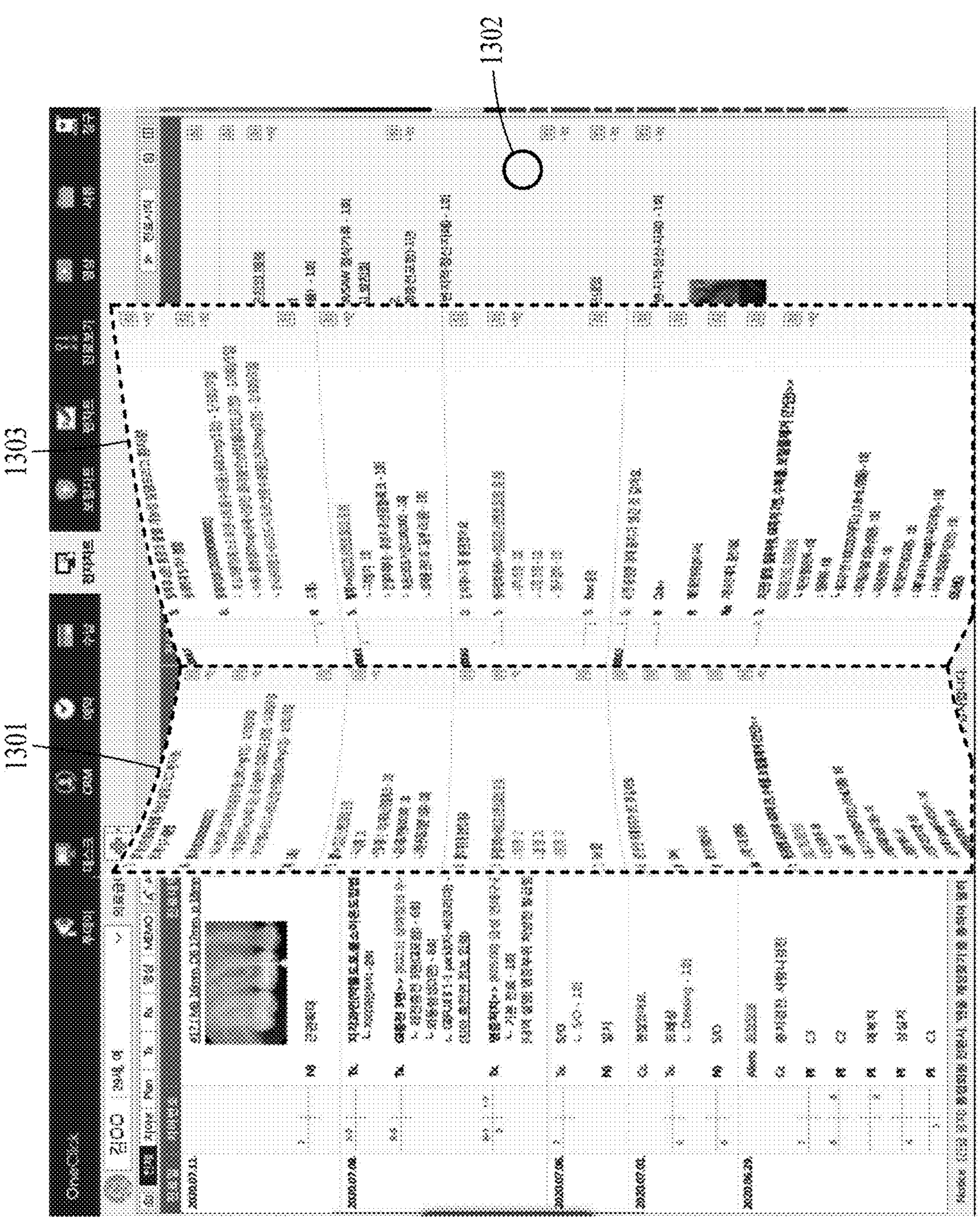
FIG. 13 is a diagram illustrating a process of switching a plurality of pages according to an interaction motion, in accordance with another example embodiment of the present disclosure.
Figure 14:
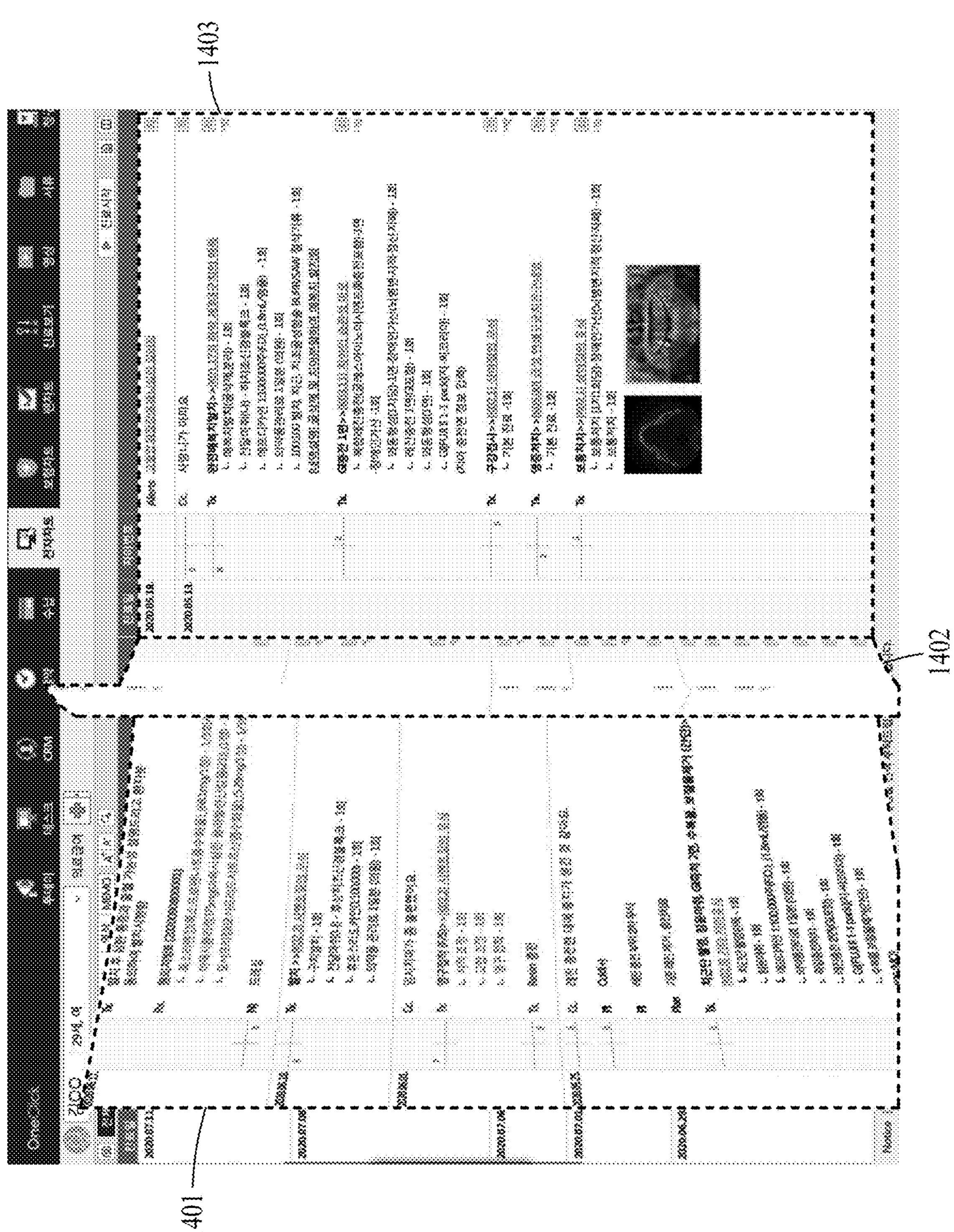
FIG. 14 is a diagram illustrating a process of switching a plurality of pages according to an interaction motion, in accordance with another example embodiment of the present disclosure.

FIGS. 12 to 14 are diagrams illustrating a process of switching a plurality of pages according to an interaction motion, in accordance with an example embodiment of the present disclosure.

Referring to FIG. 12, the computing device 101 may apply an animation effect applicable to a plurality of pages in response to the number of interaction motions detected in a certain area of an electronic chart. For example, a user may use the electronic chart to search for medical treatment details according to a medical treatment history of the user. The user may control a screen of the electronic chart such that one page or a plurality of pages are switched according to a user's search purpose.

(a) Switch a Single Page

When the user desires to search for recent medical treatment details according to a search purpose for searching the electronic chart, the user may control to switch a page corresponding to one sheet, which is because a recent record is displayed first due to the serial number automatically assigned according to the order of inputs made onto the electronic chart.

Referring to FIG. 12, the computing device 101 may detect an interaction motion 1202 corresponding to a touch applied to a certain area of an electronic chart, as a motion for switching a page of the electronic chart. The computing device 101 may apply an animation effect to a current page 1201 in response to the detected interaction motion 1202, and may thus switch the page to a next page the user desires to view.

(b) Switch a Plurality of Pages

When the date of a medical treatment to be searched for exceeds a certain period of time or when the user desires to search for specific medical treatment details performed in the past, the user may control to switch to a plurality of pages at once. In to this case, the computing device 101 may determine the number of pages to be switched at once, in consideration of the number of touches applied to a certain area of the electronic chart as the interaction operation 1202 or a time for which pressing is performed using an input device interworking with the computing device 101 after the touching is performed. In this case, the input device may include a mouse, a keyboard, a touch pen, and the like, and for the time for which the pressing is performed after the touching, a set value may be adjusted to 3 seconds, 5 seconds, 10 seconds, 30 seconds, or disabled through the electronic chart. The computing device 101 may increase the number of pages to be "skipped" as the time of being pressed by the input device increases. Conversely, the computing device 101 may reduce the number of pages to be "skipped" as the time of being pressed by the input device decreases.

For example, when the time of being pressed by the input device is 3 seconds or 5 seconds, the computing device 101 may switch two pages 1301 and 1303 according to a switching sequence, in proportion to the time according to an interaction motion 1302 as shown in FIG. 13. In this example, the computing device 101 may switch the pages at once at intervals of a predetermined time between the page 1301 and the page 1303.

For another example, when the time of being pressed by the input device is 10 seconds or 30 seconds, the computing device 101 may switch a plurality of pages 1401, 1402, and 1403 according to a switching sequence, in proportion to the time as shown in FIG. 14.

In addition, according to an example embodiment of the present disclosure, when switching pages is to be stopped at a specific point in time while a plurality of pages is being switched, the switching may be canceled in the middle of switching the pages by touching again a certain area of the electronic chart.

Figure 15:
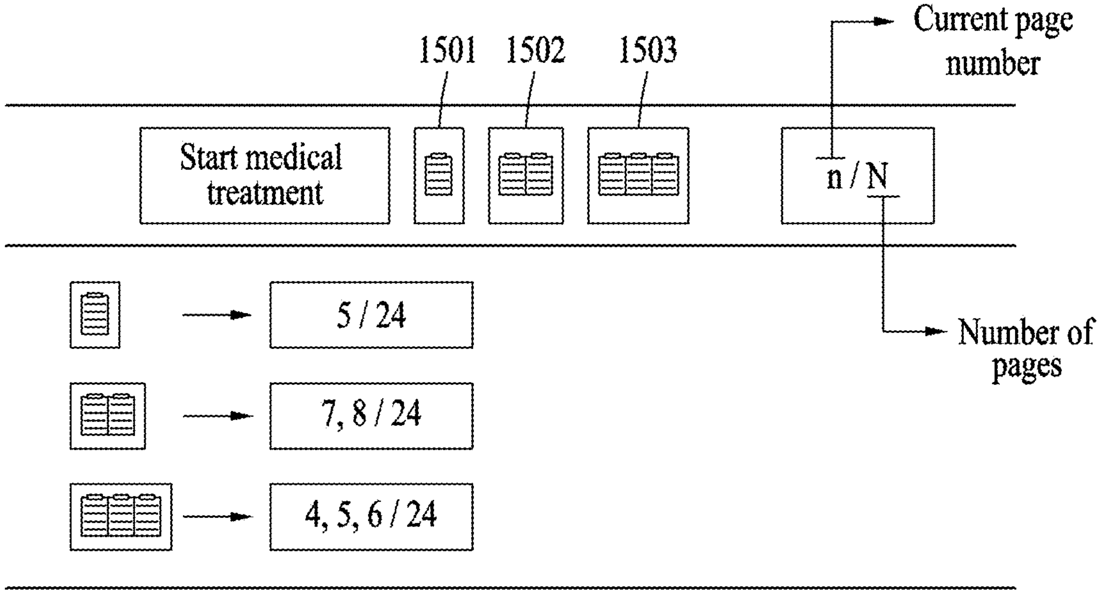
FIG. 15 is a diagram illustrating an example of visualizing a current page displayed on an electronic chart, in accordance with an example embodiment of the present disclosure.
Figure 16:
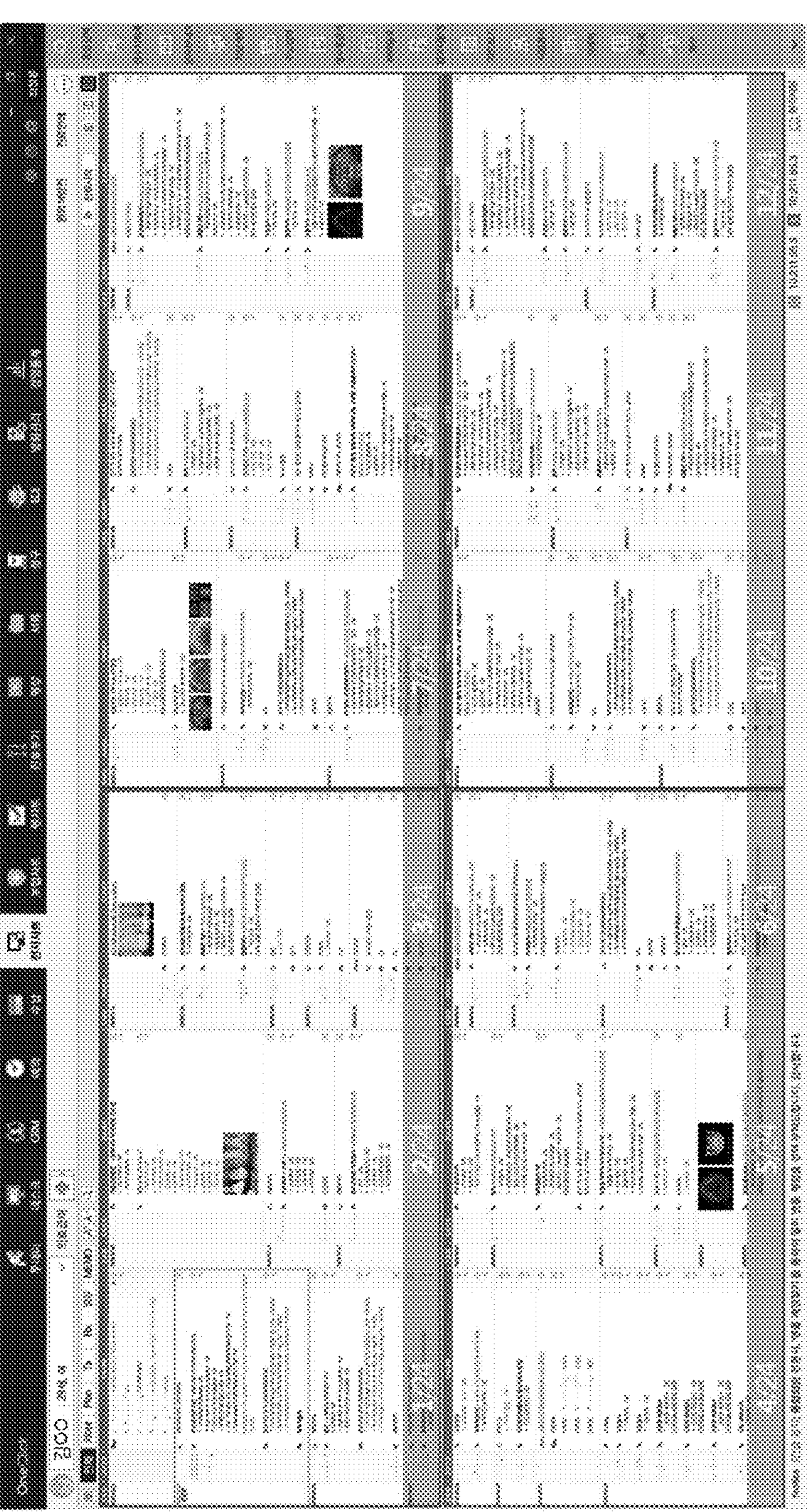
FIG. 16 is a diagram illustrating an example of visualizing a current page displayed on an electronic chart, in accordance with another example embodiment of the present disclosure.
Figure 17:
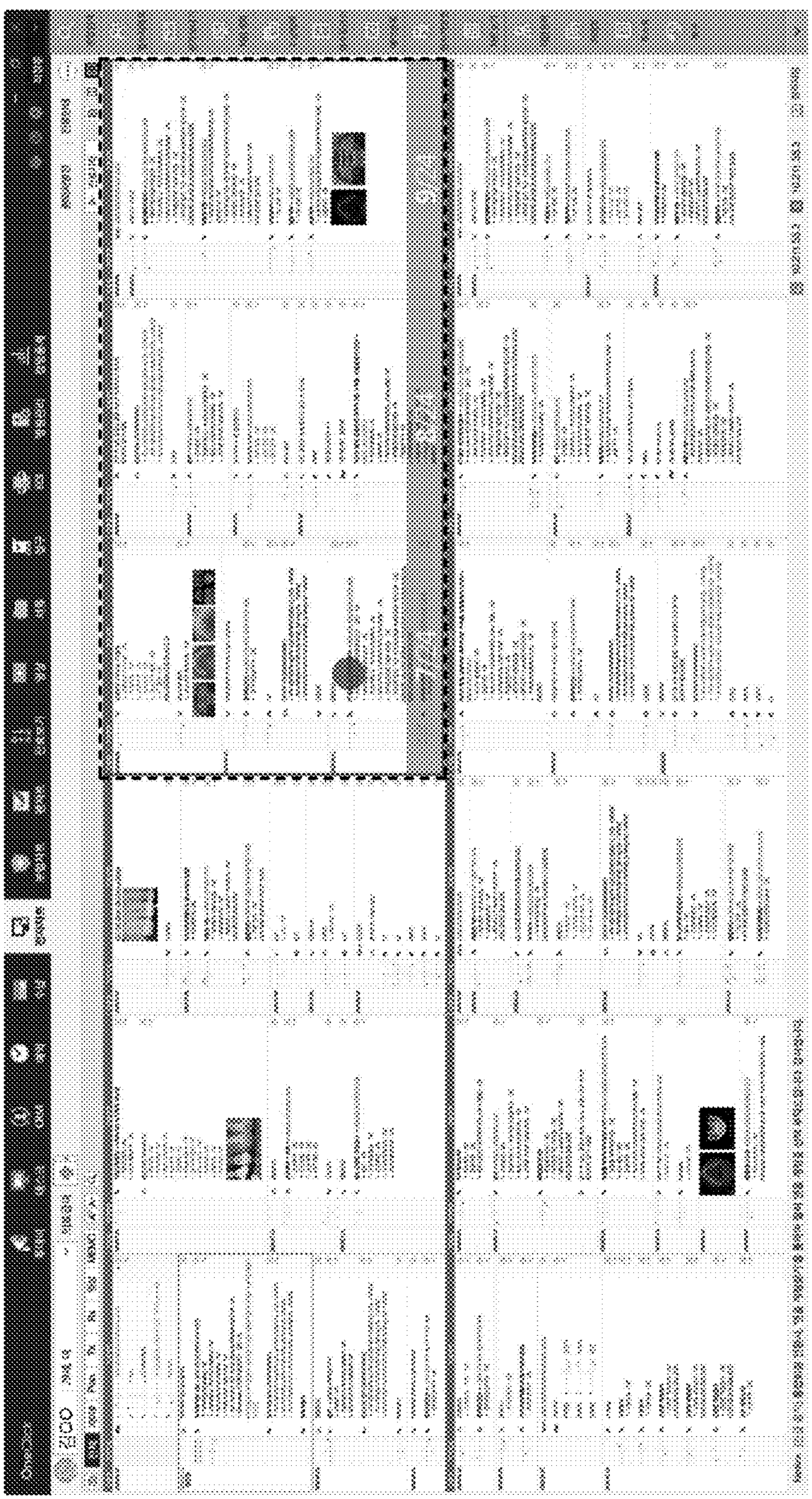
FIG. 17 is a diagram illustrating an example of visualizing a current page displayed on an electronic chart, in accordance with another example embodiment of the present disclosure.

FIGS. 15 to 17 are diagrams illustrating an example of visualizing a current page displayed on an electronic chart, in accordance with an example embodiment of the present disclosure.

Referring to FIG. 15, the computing device 101 may display a status of a current page and an identification number for each area included in a display area, in consideration of the number of areas that may be included in the display area. For example, the computing device 101 may display: (i) the total number of pages, (ii) the number of the current page, (iii) the identification number for each area included in the display area, based on the current page displayed on an electronic chart.

The computing device 101 may include icons 1501, 1502, and 1503 for setting the number of areas that may be included in the display area in a status display tab of the electronic chart. Each of the icons 1501, 1502, and 1503 may be provided in a symbolic shape for setting the number of areas included in the display area to provide medical treatment details to a user, in a search mode of the electronic chart. Each of the icons 1501, 1502, and 1503 may represent a status change in the search mode, for a visually represented purpose. That is, the icons 1501, 1502, and 1503 may induce the prediction of the number of areas included in the display area according to graphic elements such as shape and color as visual images.

For example, the icon 1501 may include visual information that induces searching the electronic chart using a display area including one area, the icon 1502 may include visual information that induces searching the electronic chart using a display area including two areas, and the icon 1503 may include visual information that induces searching the electronic chart using a display area including three areas.

The computing device 101 may identify the icon 1501, 1502, or 1503 selected by the user, and display at least one of the total number of pages, the number of a currently visualized page, or the identification number for each area included in the display area, in response to the identified icon. An area may include medical treatment details recorded in a medical treatment history of a patient that the user desires to search for, and the computing device 101 may assign an identification number to each area. The computing device 101 may display the identification number of each visualized area included in the display area, together with the total number of pages, according to the search mode of the electronic chart.

Referring to FIG. 16, when a user views a medical treatment history or more according to a set split screen, the computing device 101 may provide medical treatment details through up to 12 areas, i.e., four display areas. When the medical treatment history is visualized through a plurality of display areas, it may be difficult for the user to determine the total number of pages or the number of a current page. Therefore, the computing device 101 may set, along with the total number of pages, an identification number of an area included in a display area based on each display area. When a display area in a split screen is activated through an input device as shown in FIG. 17, the computing device 101 may display identification numbers of areas included in the activated display area, together with the total number of pages.

In addition, when the user views a medical treatment history through a split screen, the computing device 101 may additionally display a status of a current page based on the total number of pages through a status display tab of the electronic chart and may thus provide quick search convenience. That is, under the assumption that the total number of pages according to the user's medical treatment history is 24 and medical treatment details are visualized through four display areas, the number of areas displayed per page may be 12, and the number of pages that may be switched may be 2 (the number of areas/the total number of pages). Accordingly, the computing device 101 may display the status of the current page through the status display tab of the electronic chart, thereby inducing the user to classify the medical treatment details more efficiently.

Figure 18:
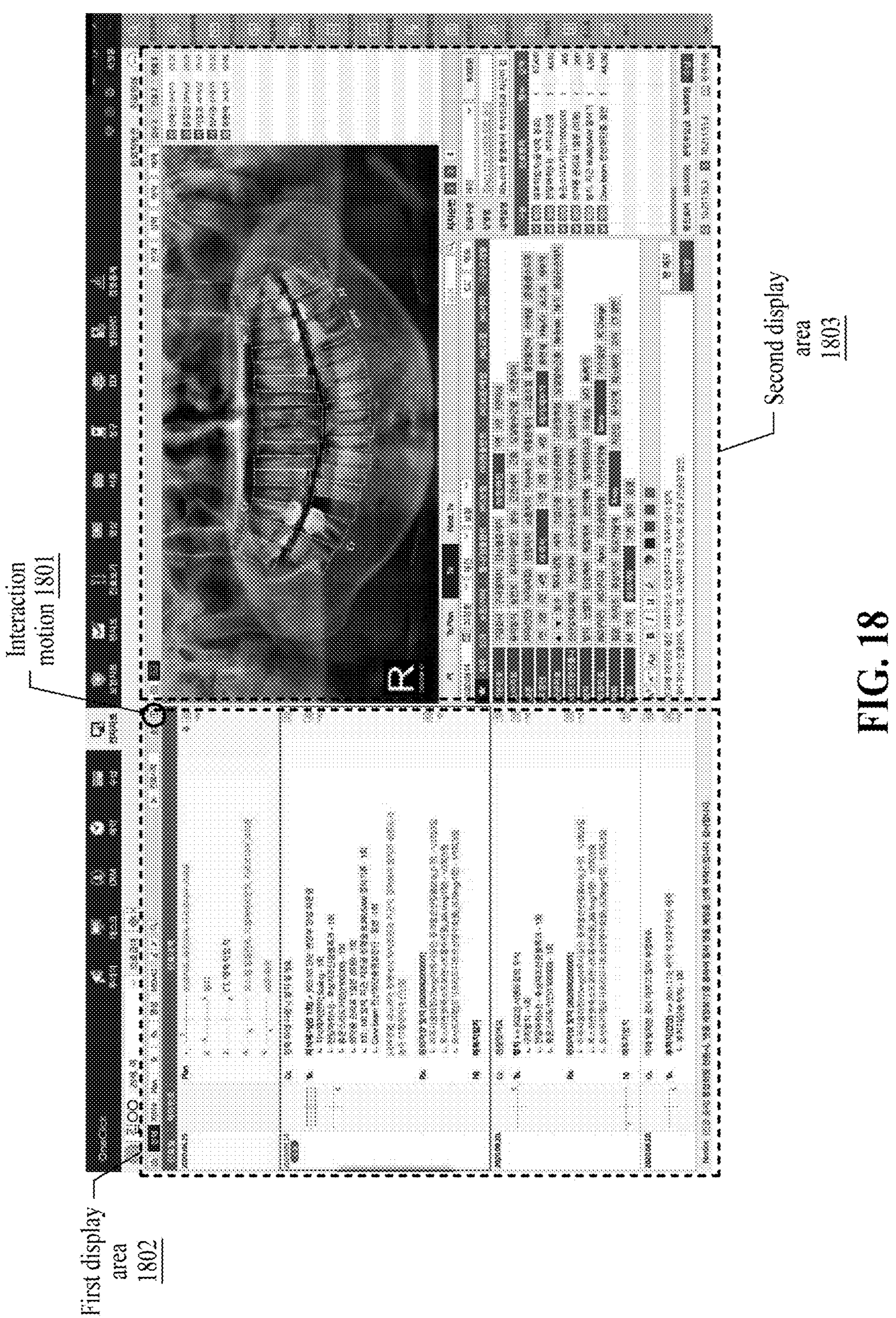
FIG. 18 is a diagram illustrating a process of variably adjusting the size of an alarm area according to an interaction motion of a user, in accordance with an example embodiment of the present disclosure.

FIG. 18 is a diagram illustrating a process of variably adjusting the size of an alarm area according to an interaction motion of a user, in accordance with an example embodiment of the present disclosure.

Referring to FIG. 18, the computing device 101 may display a first display area 1802 that displays medical treatment details according to a medical treatment history and a second display area 1803 that records an oral image of a patient and a treatment plan. Although the structure of the drawing shown in FIG. 18 is the same as the structure of displaying a display area shown in FIG. 2, the structure may be one in which medical treatment details having different formats are displayed in respective display areas. The oral image displayed on the second display area 1803 may be an image associated with the medical treatment details displayed on the first display area 1802 and, when the medical treatment details displayed on the first display area 1802 are changed, the oral image may also be changed according to the changed medical treatment details.

A user may record treatment details for the patient, the treatment plan, or the like on the electronic chart while moving the first display area 1802 displaying the medical treatment details and the second display area 1803 recording the patient's oral image and the treatment plan.

When an interaction motion 1801 for switching pages is detected from the user, the computing device 101 may apply an animation effect corresponding to the detected interaction motion 1801. The interaction motion 1801 may be a motion of selecting a split icon inserted in the electronic chart for splitting a split screen of the electronic chart or a click motion applied to a first page.

Figure 19:
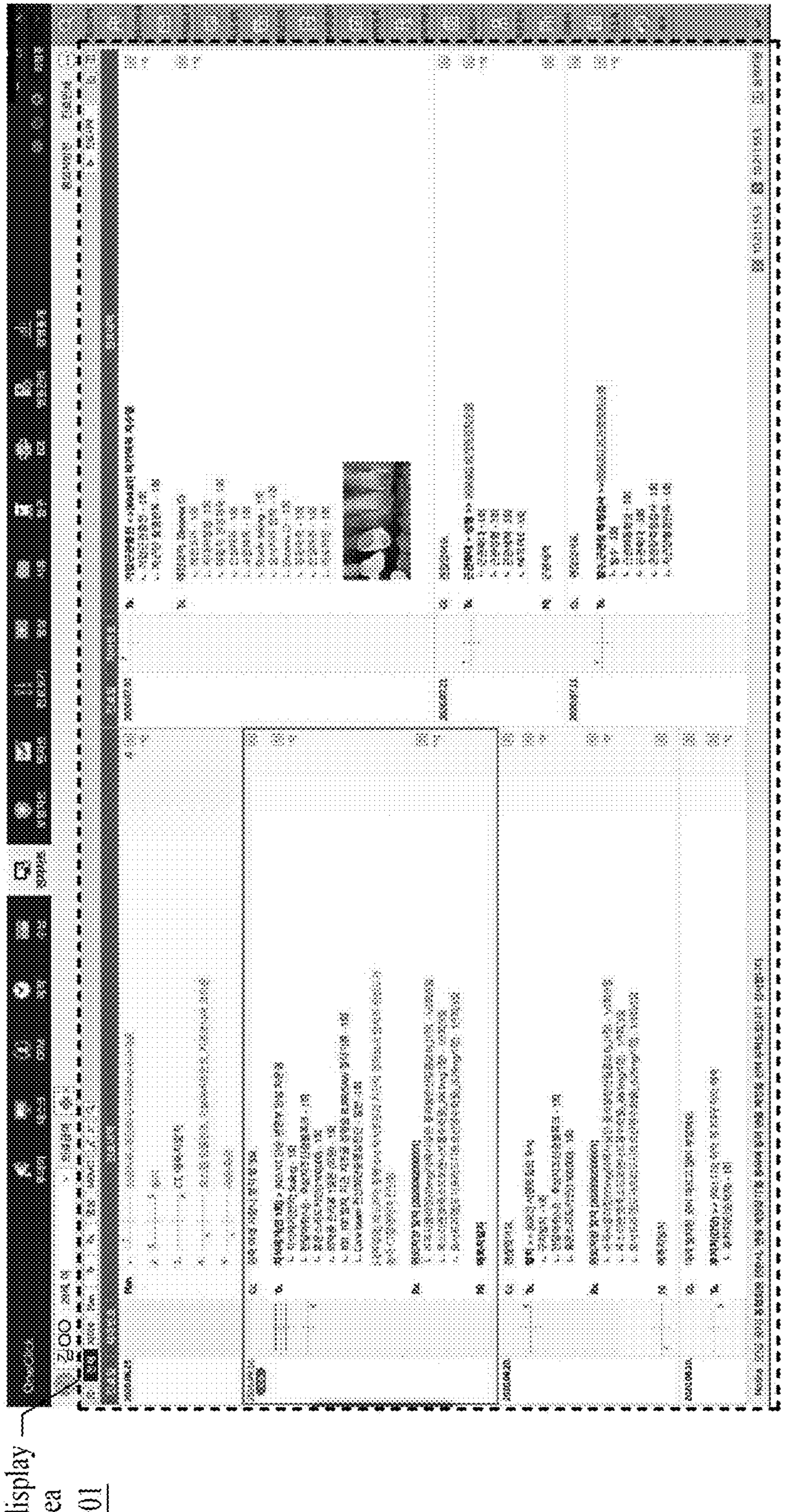
FIG. 19 is a diagram illustrating a page displayed on an electronic chart after the size of an alarm area is variably adjusted, in accordance with an example embodiment of the present disclosure.

Referring to FIG. 19, the computing device 101 may adjust the size of a first display area 1901 and the size of a second display area (not shown) in response to a detected interaction motion. The size of the first display area 1901 and the size of the second display area may be variably adjusted according to a preset ratio. Accordingly, the computing device 101 may set the second display area to be hidden in an edge area of the electronic chart according to an interaction motion and arrange the first display area 1901 in the front of the electronic chart. According to an example embodiment of the present disclosure, the arrangement between the first display area 1901 and the second display area may vary according to settings by the user.

Figure 20:
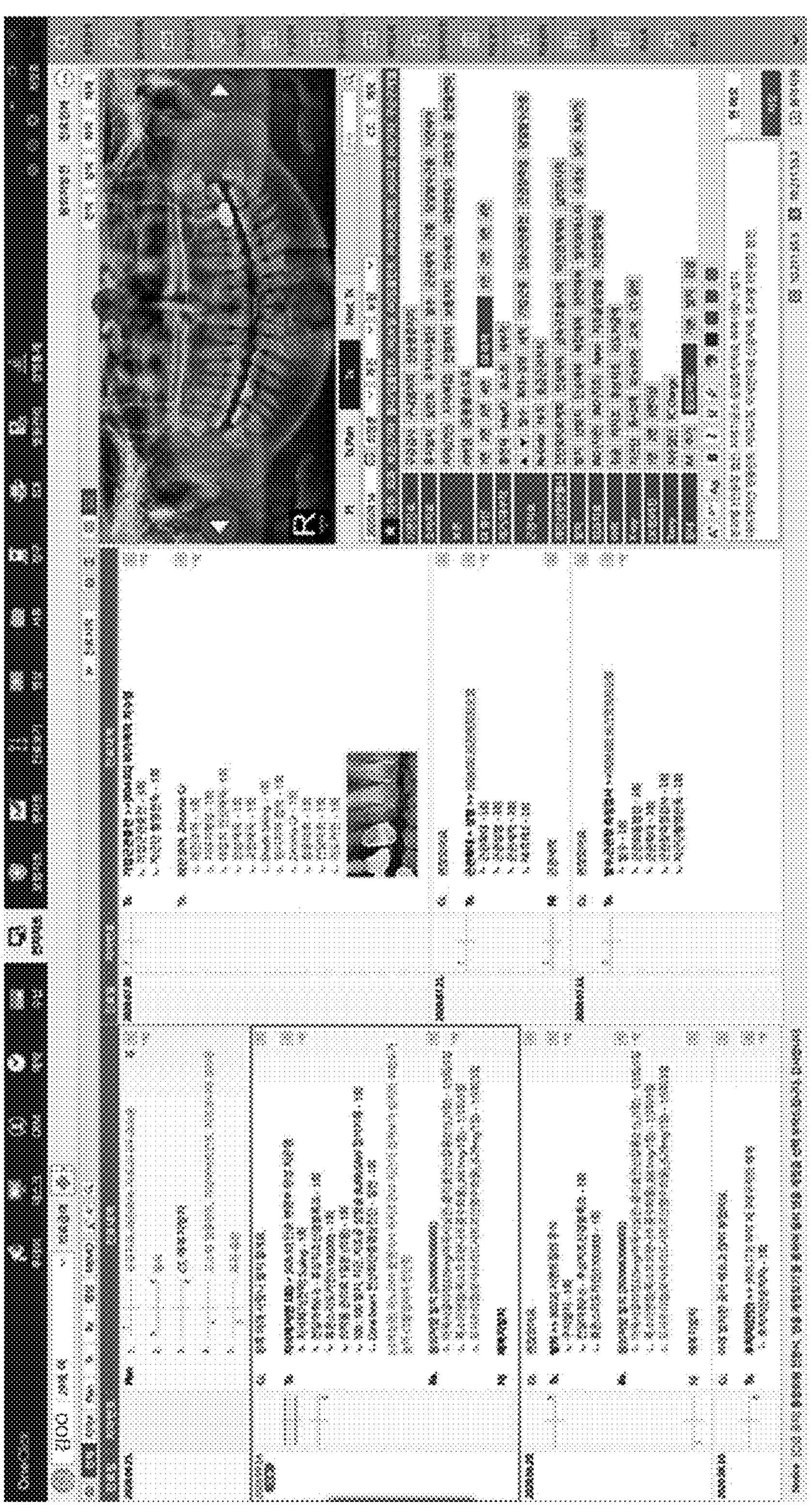
FIG. 20 is a diagram illustrating an operation of switching an oral image according to an interaction motion, in accordance with an example embodiment of the present disclosure.
Figure 21:
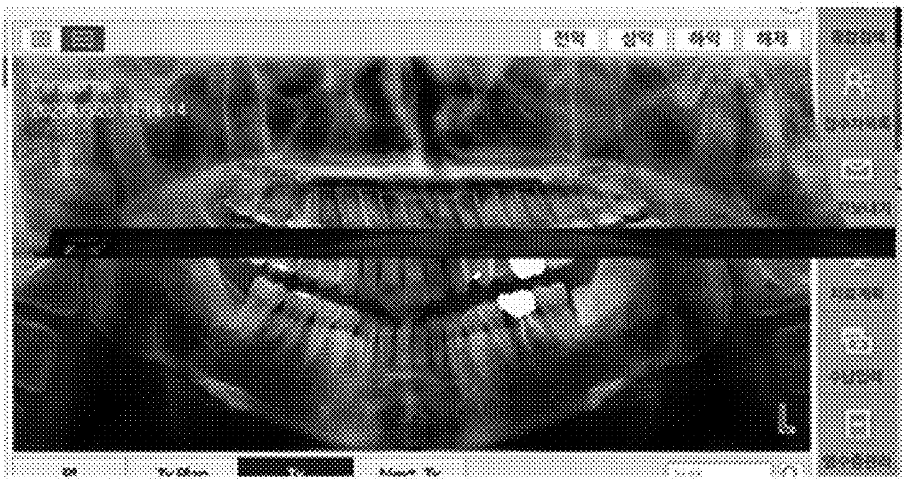
FIG. 21 is a diagram illustrating types to which an oral image is switched, in accordance with an example embodiment of the present disclosure.
Figure 21:
Figure 21:
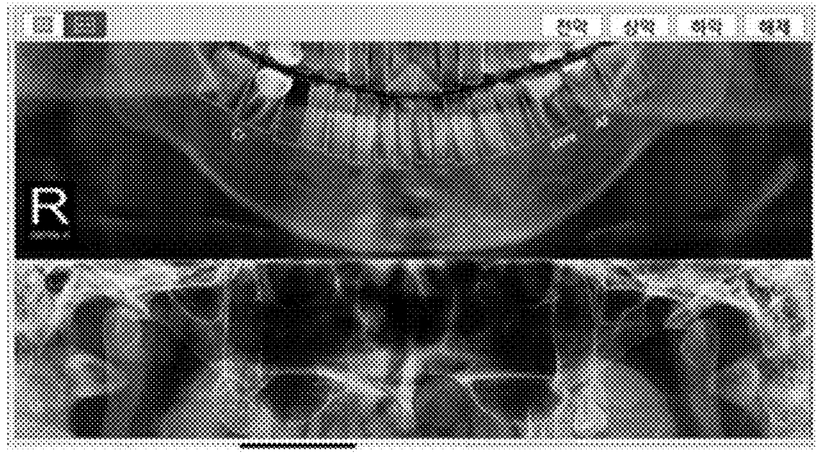

FIGS. 20 and 21 are diagrams illustrating an operation of switching an oral image according to an interaction motion, in accordance with an example embodiment of the present disclosure.

Referring to FIG. 20, the computing device 101 may change and display an oral image in association with medical treatment details displayed on a first display area. That is, the computing device 101 may change and display the oral image by applying an animation effect to the oral image in response to an interaction motion detected in the first display area of an electronic chart. In this case, the interaction motion may be a motion performed by the user to click on the medical treatment details recorded in the first display area.

The computing device 101 may change and display the oral image in response to an interaction motion applied to an oral image displayed on a second display area. The computing device 101 may detect an interaction motion applied to an edge of a first oral image displayed on the second display area of the electronic chart. The computing device 101 may determine an animation effect for switching the first oral image in different directions in response to the detected interaction motion. The computing device 101 may switch the first oral image to a second oral image and display the second oral image by applying the animation effect to the first oral image.

Referring to FIG. 21, the computing device 101 may switch oral images according to various animation effects. The computing device 101 may detect an interaction motion applied to an edge of a first oral image including, for example, up, down, left, right, and diagonal lines. The computing device 101 may switch the oral images by applying (1) an animation effect by which an oral image is turned leftward/rightward/upward/downward, (2) an animation effect by which an oral image slides from bottom to top or from top to bottom, or (3) an animation effect by which an oral image is turned diagonally, in consideration of a position of each edge at which an interaction motion is detected.

Figure 22:
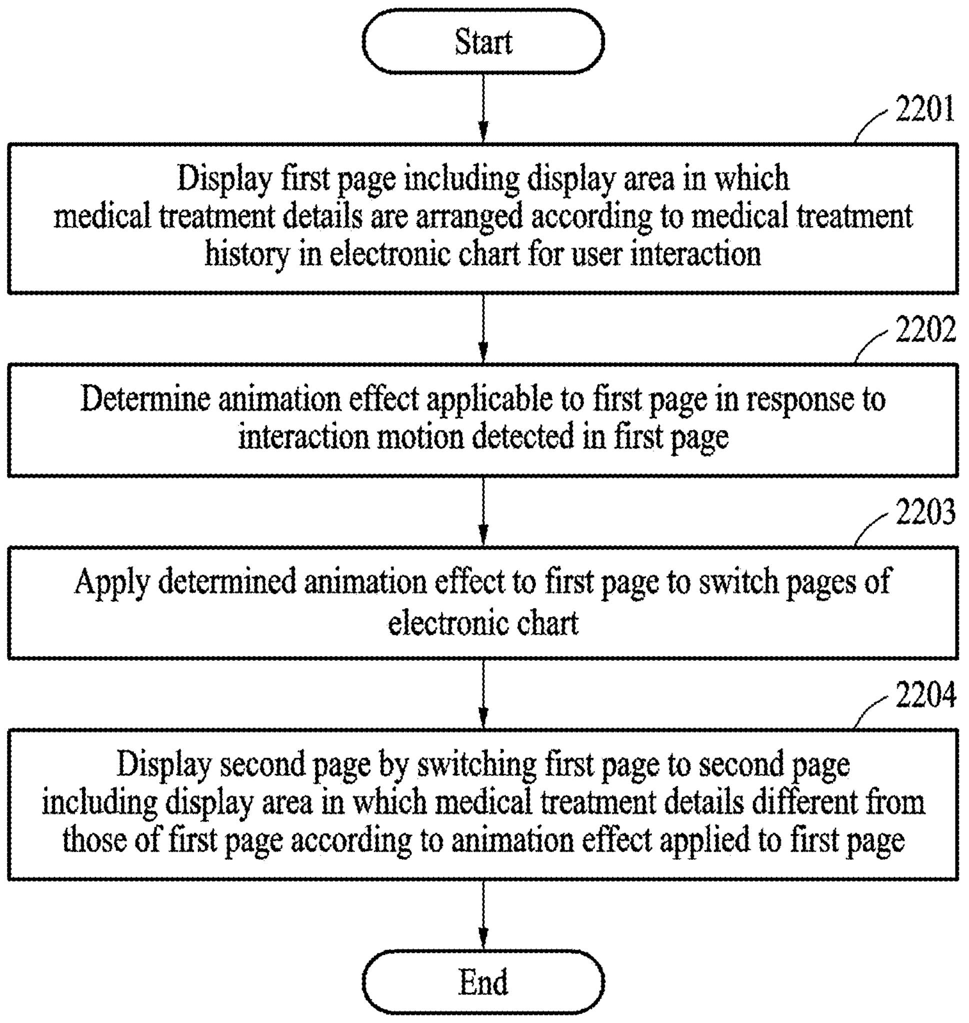
FIG. 22 is a flowchart illustrating a page turning method, in accordance with an example embodiment of the present disclosure.

FIG. 22 is a flowchart illustrating a page turning method, in accordance with an example embodiment of the present disclosure.

In operation 2201, a computing device may display a first page including a display area in which medical treatment details are arranged according to a medical treatment history in an electronic chart for user interaction. The computing device may display the first page in which at least one display area is grouped to correspond to a split screen of the electronic chart for viewing the medical treatment details. The display area may be split into a plurality of areas for arranging the medical treatment details.

In operation 2202, the computing device may determine an animation effect applicable to the first page in response to an interaction motion detected on the first page. The computing device may detect an interaction motion applied to an edge of the display area included in the first page and determine an animation effect for switching the first page in different directions according to a position of the edge. The computing device may determine the animation effect by which a screen switching range of a page to be displayed on the electronic chart is variably adjusted in response to the number of grouped display areas.

The computing device may determine the animation effect for switching the first page in consideration of at least one of a separation distance between a first position where the interaction motion is detected and a second position detected by a movement from the first page relative to the first position, or a moving direction.

In operation 2203, the computing device may apply the determined animation effect to the first page to switch pages of the electronic chart.

In operation 2204, the computing device may display a second page by switching from the first page to the second page including a display area in which medical treatment details different from those of the first page are arranged, according to the animation effect applied to the first page. The computing device may apply a folding effect by which the first page is folded according to the animation effect, and display the second page using a back side of the first page to which the folding effect is applied and another side connected to the back side.

Figure 23:
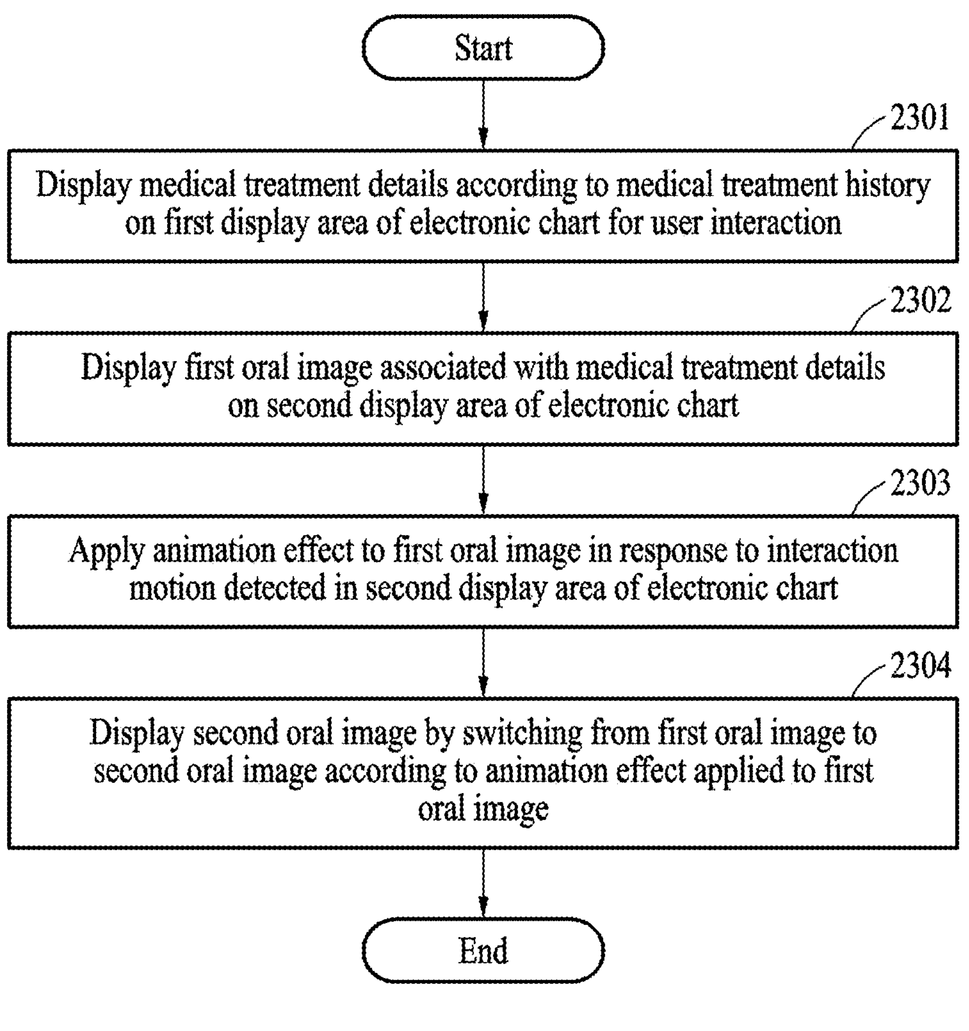
FIG. 23 is a flowchart illustrating a page turning method, in accordance with another example embodiment of the present disclosure.

FIG. 23 is a flowchart illustrating a page turning method, in accordance with another example embodiment of the present disclosure.

In operation 2301, a computing device may display medical treatment details according to a medical treatment history on a first display area of an electronic chart for user interaction.

In operation 2302, the computing device may display a first oral image associated with the medical treatment details on a second display area of the electronic chart. The computing device may display the first oral image on the second display area in which the size of the first display area and the size of the second display area are variably adjusted to correspond to a split screen of the electronic chart.

In operation 2303, the computing device may apply an animation effect to the first oral image in response to an interaction motion detected in the second display area of the electronic chart. The computing device may detect an interaction motion applied to an edge of the second display area of the electronic chart and determine an animation effect for switching the first oral image in a different direction corresponding to a position of the edge.

In operation 2304, the computing device may display a second oral image by switching from the first oral image to the second oral image according to the animation effect applied to the first oral image.

The page turning method according to various example embodiments of the present disclosure that detects user interaction applied to an electronic chart and applies an animation effect according to the detected user interaction to switch and display pages of the electronic chart may be written as a program executable in a computer and implemented in various recording media such as magnetic storage media, optical reading media, and digital storage media.

The example embodiments described herein may be implemented using a hardware component, a software component, and/or a combination thereof. A processing device may be implemented using one or more general-purpose or special-purpose computers, such as, for example, a processor, a controller, and an arithmetic logic unit (ALU), a DSP, a microcomputer, a field-programmable gate array (FPGA), a programmable logic unit (PLU), a microprocessor, or any other device capable of responding to and executing instructions in a defined manner. The processing device may run an operating system (OS) and one or more software applications that run on the OS. The processing device may also access, store, manipulate, process, and create data in response to execution of the software. For purpose of simplicity, the description of a processing device is singular; however, one of ordinary skill in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or one or more combinations thereof, to independently or collectively instruct or configure the processing device to operate as desired. The software and/or data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums. The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs and/or DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher-level code that may be executed by the computer using an interpreter.

The above-described devices may be configured to act as one or more software modules in order to perform the operations of the above-described examples, or vice versa.

Although the present disclosure includes details of a plurality of specific example embodiments, the details should not be construed as limiting any claimed matter or a scope of claims, but should be construed as being descriptions of features that may belong to specific example embodiments. The specific features described in the present disclosure in the context of example embodiments may be combined and implemented in a single example embodiment. On the contrary, various features described in the context of a single example embodiment may also be implemented in a plurality of example embodiments or in any appropriate sub-combinations. Moreover, although features have been described above in specific combinations and even initially claimed as such, one or more features from a claimed combination may be excluded from the combination, and the claimed combination may be changed to a sub-combination or a modification of a sub-combination.

Likewise, although operations are described in a predetermined order with reference to the drawings, it should not be construed that the operations need to be performed sequentially or in the predetermined order, which is illustrated to obtain a desirable result, or that all of the shown operations need to be performed. In specific cases, multitasking and parallel processing may be advantageous. In addition, it should not be construed that the separation of various device components of the example embodiments is required in all types of example embodiments, and it should be understood that the described program components and devices are generally integrated as a single software product or packaged into a multiple-software product.

The example embodiments described in the present disclosure and the drawings are intended to present specific examples only in order to aid in understanding the to present disclosure, but are not intended to limit the scope of the present disclosure. It will be apparent to one of ordinary skill in the art that various modifications based on the technical spirit of the present disclosure, in addition to the disclosed example embodiments, may be made.

The invention claimed is:

1. A page turning method, comprising:

displaying a first page comprising a display area in which medical treatment details are arranged according to a medical treatment history on an electronic chart for user interaction, wherein the medical treatment details comprise treatment details recorded in a medical treatment history of a patient and are sequentially arranged according to the medical treatment history such that a more recent record is displayed first due to the serial number automatically assigned according to the order of inputs made onto the electronic chart;

determining an animation effect applicable to the first page in response to an interaction motion detected on the first page;

applying the determined animation effect to the first page to switch pages of the electronic chart; and displaying a second page by switching from the first page to the second page comprising a display area in which medical treatment details different from those of the first page are arranged, according to the animation effect applied to the first page;

wherein the determining of the animation effect comprises:

determining a number of pages to which the animation effect is to be applied, in consideration of a time for which pressing is performed using an input device interworking with the computing device after a touch is applied to a certain area of the electronic chart as the interaction motion; and automatically switching, without further user input after the interaction motion is detected, a plurality of pages corresponding to the determined number of pages according to a switching sequence between a current page and a target page corresponding to the determined number of pages at once at intervals of a predetermined time;

wherein the determining of the animation effect further comprises determining the animation effect that adjusts a size of the first page to allow full view or detailed view, wherein the full view includes a plurality of display areas and provides overall change in the medical treatment details according to the medical treatment history, and the detailed view includes one display area and provides in detail medical treatment details of the medical treatment history; and wherein the applying of the determined animation effect further comprises switching the first page to the detailed view or the full view while displaying the second page overlapping the first page, in the form of a background for the first page to which the animation effect that adjusts the size of the first page is applied, wherein the first page and the second page comprise sequentially arranged medical treatment details according to the medical treatment history.

2. The page turning method of claim 1, wherein the displaying of the first page comprises:

displaying the first page in which at least one display area is grouped in response to a split screen of the electronic chart to view the medical treatment details.

3. The page turning method of claim 2, wherein the determining of the animation effect comprises:

determining an animation effect by which a screen switching range of a page displayed on the electronic chart is variably adjusted in response to the number of grouped display areas.

4. The page turning method of claim 1, wherein the determining of the animation effect comprises:

detecting an interaction motion applied to an edge of the display area comprised in the first page, and determining an animation effect for switching the first page in a different direction according to a position of the edge.

5. The page turning method of claim 1, wherein the determining of the animation effect comprises:

determining an animation effect for switching the first page, in consideration of a moving direction of the interaction motion.

6. The page turning method of claim 1, wherein the determining of the animation effect comprises:

determining a switching speed of the first page based on a separation distance between a first position at which the interaction motion is detected and a second position detected as moved on the first page based on the first position.

7. The page turning method of claim 1, wherein the display area is split into a plurality of areas for arranging the medical treatment details, wherein, to each of the plurality of areas, an identification number is assigned to distinguish the medical treatment details visualized on the electronic chart based on a total number of pages.

8. The page turning method of claim 1, wherein the displaying of the second page comprises:

displaying the second page by applying a folding effect of folding the first page according to the animation effect and by using a back side of the first page to which the folding effect is applied and another side connected to the back side.

9. The method of claim 1, wherein determining the number of pages includes increasing the number of pages in response to the amount of time increasing.

10. The page turning method of claim 1, wherein the determining of the animation effect further comprises stopping the switching in the middle of switching the plurality of pages when a touch on a specific area of the electronic chart is received again while the plurality of pages is being switched.

11. A computing device comprising a processor and non-transitory computer readable media containing machine-executable instructions for performing the method of claim 1, wherein the processor is configured to execute the machine-executable instructions.

12. The computing device of claim 11, wherein the machine-executable instructions for displaying of the first page comprise machine-executable instructions for displaying the first page in which at least one display area is grouped in response to a split screen of the electronic chart to view the medical treatment details.

13. The computing device of claim 12, wherein the machine-executable instructions for determining of the animation effect comprise machine-executable instructions for determining an animation effect by which a screen switching range of a page displayed on the electronic chart is variably adjusted in response to the number of grouped display areas.

14. The computing device of claim 11, wherein the machine-executable instructions for determining of the animation effect comprise machine-executable instructions for detecting an interaction motion applied to an edge of the display area comprised in the first page, and determining an animation effect for switching the first page in a different direction according to a position of the edge.

15. The computing device of claim 11, wherein the machine-executable instructions for determining of the animation effect comprise machine-executable instructions for determining an animation effect for switching the first page, in consideration of a moving direction of the interaction motion.

16. The computing device of claim 11, wherein the machine-executable instructions for determining of the animation effect comprise machine-executable instructions for determining a switching speed of the first page based on a separation distance between a first position at which the interaction motion is detected and a second position detected as moved on the first page based on the first position.

17. The computing device of claim 11, wherein the display area is split into a plurality of areas for arranging the medical treatment details, wherein, to each of the plurality of areas, an identification number is assigned to distinguish the medical treatment details visualized on the electronic chart based on a total number of pages.

18. The computing device of claim 11, wherein the machine-executable instructions for displaying of the second page comprise machine-executable instructions for displaying the second page by applying a folding effect of folding the first page according to the animation effect and by using a back side of the first page to which the folding effect is applied and another side connected to the back side.

19. The computing device of claim 11, wherein the machine-executable instructions include machine-executable instructions for increasing the number of pages in response to the amount of time increasing.

* * * * *